United States Patent [19]
Uchida et al.

[11] Patent Number: 5,521,097
[45] Date of Patent: May 28, 1996

[54] METHOD OF DETERMINING AMINO ACID SEQUENCE OF PROTEIN OR PEPTIDE FROM CARBOXY-TERMINAL

[75] Inventors: Toyoaki Uchida, Tokyo; Akira Tsugita, Kashiwa; Keiji Takamoto, Nagareyama; Kazuo Satake, Kawasaki, all of Japan

[73] Assignee: Seiko Instruments Inc., Japan

[21] Appl. No.: 931,931

[22] Filed: Aug. 18, 1992

[30] Foreign Application Priority Data

Aug. 28, 1991 [JP] Japan ................................ 3-217437
Nov. 15, 1991 [JP] Japan ................................ 3-300818

[51] Int. Cl.$^6$ ................................................. G01N 33/00
[52] U.S. Cl. ............................. 436/86; 436/89; 436/173; 530/334; 530/342; 530/343; 530/344; 530/402; 530/412
[58] Field of Search ........................... 436/86, 89, 173; 530/333, 334, 342, 343, 344, 402, 412; 250/282

[56] References Cited

U.S. PATENT DOCUMENTS

| | | | |
|---|---|---|---|
| 4,701,419 | 10/1987 | Morris | 436/89 |
| 4,820,648 | 4/1989 | Caprioli et al. | 436/89 |
| 5,104,973 | 4/1992 | Kondo et al. | 530/334 |
| 5,185,266 | 2/1993 | Boyd et al. | 436/89 |

FOREIGN PATENT DOCUMENTS

| | | |
|---|---|---|
| 0257735 | 3/1988 | European Pat. Off. |
| 8908835 | 9/1989 | WIPO |

OTHER PUBLICATIONS

Orlovska et al., "Use of trifluoroacetic acid and its anhydride for studying the N-terminal sequence of amino acids in proteins", Chemical Abstracts, vol. 70, No. 1 (1969), p. 68.

Hawke et al., "Microsequence Analysis of Peptides and Proteins: Trimethyl–silylisothiocyanate as a Reagent for COOH–Terminal Sequence Analysis", Analytical Biochemistry, vol. 166, No. 2, Nov. 1, 1987, pp. 298–307.

Tsugita et al., "Reaction of Pentafluoropropionic Anhydride Vapor on Polypeptide as Revealed by Mass Spectrometry. A Carboxypeptidase Mimetic Degradation", Chemistry Letters, vol. 2, 1992, pp. 235–238.

Tsugita et al., "Exopeptidase Digestion in Combination with Field Desorption Mass Spectrometry for Amino Acid Sequence Determination", FEBS Letters, vol. 137, No. 1, Jan. 1982, pp. 19–24.

Primary Examiner—David A. Redding
Attorney, Agent, or Firm—Adams & Wilks

[57] ABSTRACT

A protein or peptide is treated by a vapor containing an organic acid represented by the following general formula $CF_3$—$(CF_2)n$—COOH (n is zero or more integer). The resulting reaction mixture is processed by a mass spectrometer to obtain a mass spectrum to measure a mass of respective chemical species contained in the reaction mixture. Alternatively, the reaction mixture is processed by an amino acid analyzer to determine an amino acid sequence of the protein or peptide from the carboxy-terminal. According to another method, the protein or peptide is treated by an anhydride of the organic acid represented by the following general formula $CF_3$—$(CF_2)n$—COOH (n is zero or more integer). The resulting reaction mixture is processed by a mass spectrometer to obtain a mass spectrum to measure a mass of respective chemical species contained in the reaction mixture to determine an amino acid sequence of the protein or peptide from the carboxy-terminal.

19 Claims, 25 Drawing Sheets

FIG. 1
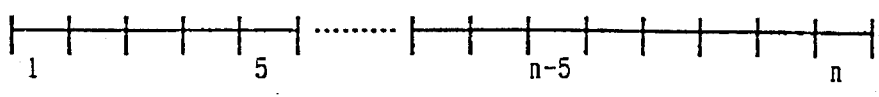
PROTEIN OR PEPTIDE
| TRIFLUOROACETIC ACID(CF-COOH),
| PENTAFLUORPROPIONIC ACID(CF-CF-COOH), OR
↓ PHEPTAFLUOROBUTYLIC ACID(CF-CF-CF-COOH)
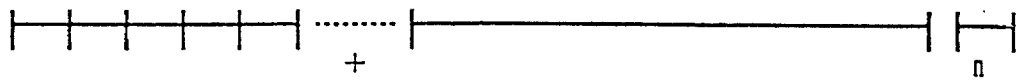
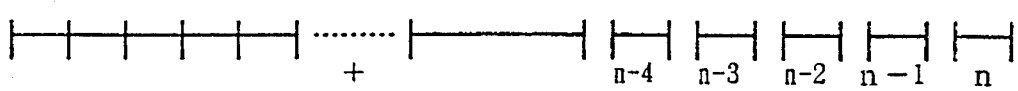
⋮
↓
TO FAST ATOM BOMBORDMENT MASS SPECTROMETER(FAB-MS),
ELECTRO-SPRAY IONIZATON MASS SPECTROMETER(FSI-MS),
OR AMINO ACID ANALYZER

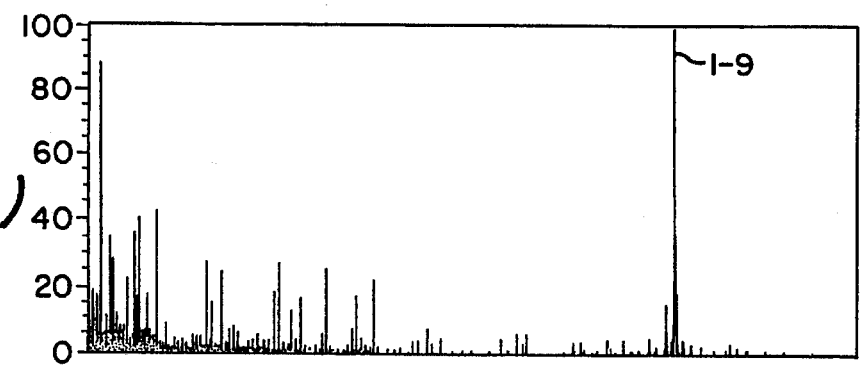
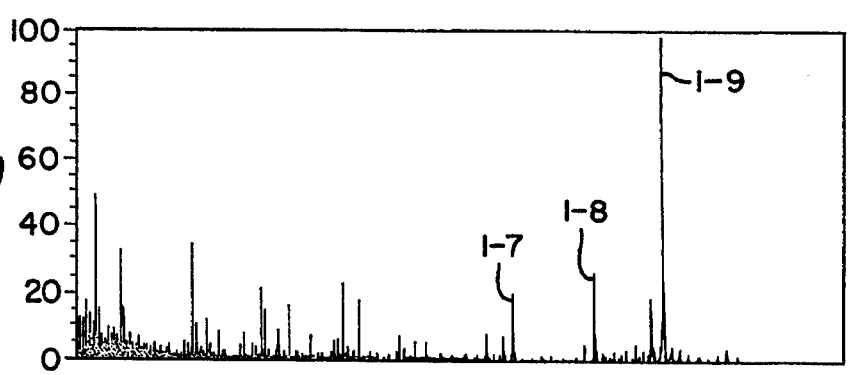
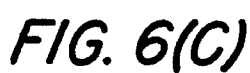
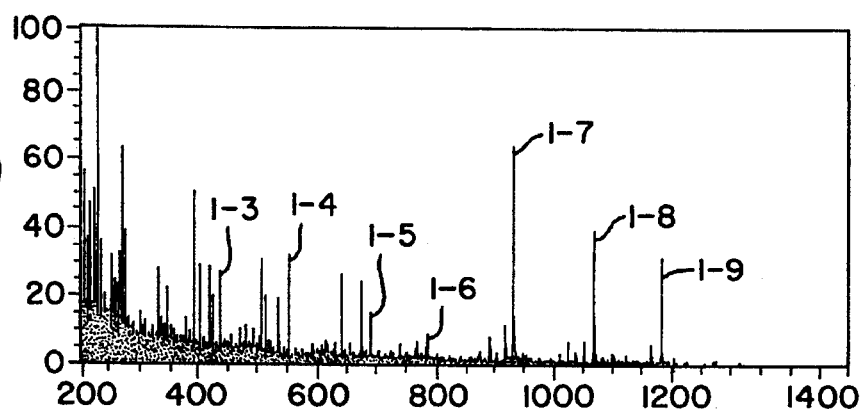

FIG. 12
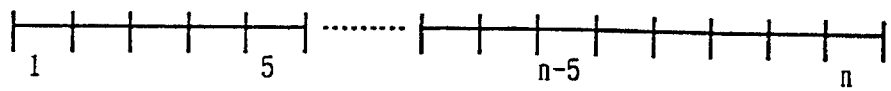
PROTEIN OR PEPTIDE
| TRIFLUOROACETIC ACID ANHYDRID(CF-COOH),
| PENTAFLUORPROPIONIC ACID ANHYDRID(CF-CF-COOH), OR
↓ PHEPTAFLUOROBUTYLIC ACID ANHYDRID(CF-CF-CF-COOH)
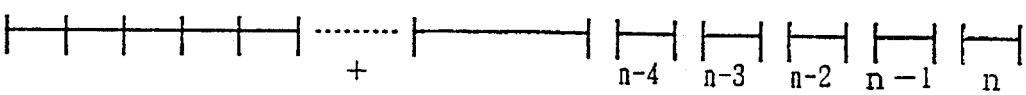
TO FAST ATOM BOMBORDMENT MASS SPECTROMETER(FAB-MS)

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
        ( A ) LENGTH: 6
        ( B ) TYPE: amino acid
        ( C ) STRANDEDNESS:
        ( D ) TOPOLOGY: linear chain ( x i ) SEQUENCE DESCRIPTION: SEQ ID NO: 1:

Leu  Trp  Met  Arg  Phe  Ala
        1                         5

( 2 ) INFORMATION FOR SEQ ID NO: 2:

( i ) SEQUENCE CHARACTERISTICS:
        ( A ) LENGTH: 9

-continued (B) TYPE: amino acid
(C) STRANDEDNESS:
(D) TOPOLOGY: linear chain (x i) SEQUENCE DESCRIPTION: SEQ ID NO: 2:

Arg Val Tyr Ile His Pro Phe His Leu
1               5

(2) INFORMATION FOR SEQ ID NO: 3:

(i) SEQUENCE CHARACTERISTICS:
(A) LENGTH: 8
(B) TYPE: amino acid
(C) STRANDEDNESS:
(D) TOPOLOGY: linear chain (x i) SEQUENCE DESCRIPTION: SEQ ID NO: 3:

His Pro Phe His Leu Leu Val Tyr
1               5

(2) INFORMATION FOR SEQ ID NO: 4:

(i) SEQUENCE CHARACTERISTICS:
(A) LENGTH: 23
(B) TYPE: amino acid
(C) STRANDEDNESS:
(D) TOPOLOGY: linear chain (x i) SEQUENCE DESCRIPTION: SEQ ID NO: 4:

Gly Ile Gly Lys Phe Leu His Ser Ala Gly Lys Phe Gly Lys Ala
            5                   10                  15
Phe Val Gly Glu Ile Met Lys Ser
            20

(2) INFORMATION FOR SEQ ID NO: 5:

(i) SEQUENCE CHARACTERISTICS:
(A) LENGTH: 8
(B) TYPE: amino acid
(C) STRANDEDNESS:
(D) TOPOLOGY: linear chain (x i) SEQUENCE DESCRIPTION: SEQ ID NO: 5:

Lys Lys Lys His Pro Asp Tyr Ile
1               5

(2) INFORMATION FOR SEQ ID NO: 6:

(i) SEQUENCE CHARACTERISTICS:
(A) LENGTH: 12
(B) TYPE: amino acid
(C) STRANDEDNESS:
(D) TOPOLOGY: linear chain (x i) SEQUENCE DESCRIPTION: SEQ ID NO: 6:

Ala Arg Gly Ile Lys Gly Ile Arg Gly Phe Ser Gly
1               5                   10

METHOD OF DETERMINING AMINO ACID SEQUENCE OF PROTEIN OR PEPTIDE FROM CARBOXY-TERMINAL

BACKGROUND OF THE INVENTION

The present invention relates to the method of analyzing a primary structure of protein or peptide.

Conventionally, in order to determine an amino acid sequence of protein or peptide from a carboxy-terminal or C-terminal, as shown in FIG. 2, carboxypeptidase is applied to protein or peptide. Then, a digested solution is sampled time-sequentially, and the sampled digested solution is analyzed by an amino acid analyzer to effect quantitative measurement of free amino acids. Such method is described in "Biochemical Experiment Text, Vol. 1, Chemistry of Protein II, pp 203–211, 1976, edited by Japanese Biochemistry Society".

There has been reported another method that the digested solution is treated by a mass spectrometer to measure mass of protein or peptide which partially lost amino acids from the C-terminal. Such method is disclosed in "A. Tsugita, R. van den Broek, M. Pyzybylski, FEBS. Lett. 137, 19(1982)".

Further, there has been reported a still another method in "D. H. Hawke, H-. W. Lahm, J. E. Shively, C. W. Todd, Anal. Biochem. 166, 298(1987)". As shown in FIG. 3, the C-terminal is activated by acetic acid anhydride and is then coupled to trimethylsililisothiocyanate (TMS-ITC). Thereafter, the protein or peptide is cut by hydrochloric acid. These sequential treatments are repeatedly undertaken to perform the amino acid sequence analysis.

The conventional method utilizing carboxypeptidase has drawbacks that the substrate specificity and the activity of the carboxypeptidase vary dependently on a C-terminal amino acid or an adjacent amino acid; that the reagent contains other contaminant enzymes which hinder a precise analysis; and that an external amino acid is introduced by self-dissociation of the enzyme to thereby hinder sensitivity of the amino acid analysis. The other conventional method utilizing TMS-ITC has drawbacks that the processing is complicated since three kinds of reagents are applied sequentially and that repititive yield rate is rather small, thereby not being practical.

SUMMARY OF THE INVENTION

Therefore, an object of the invention is to provide a simplified method of determining amino acid sequence of the protein or peptide from a C-terminal without using an enzyme or other complicated organic compounds.

According to a first aspect of the invention, in order to undertake the analysis of the amino acid sequence from the C-terminal while removing the above noted drawbacks, the protein or peptide is treated by a specific organic acid represented by the following general formula: $CF_3—(CF_2)n—COOH$ (n is zero or more integer), such as trifluoroacetic acid (n=0), pentafluoropropionic acid (n=1) and heptafluorobutyric acid (n=2). By such operation, the amino acid sequence can be determined from the C-terminal of the protein or peptide by simplified treatment without utilizing an enzyme.

According to a second aspect of the invention, in order to undertake the analysis of the amino acid sequence from the C-terminal while removing the above noted drawbacks, the protein or peptide is treated by an anhydride of the specific organic acid represented by the following general formula: $CF_3—(CF_2)n—COOH$ (n is zero or more integer), such as anhydrides of trifluoroacetic acid (n=0), pentafluoropropionic acid (n=1) and heptafluorobutyric acid (n=2). By such operation, the amino acid sequence can be determined from the C-terminal of the protein or peptide by simplified treatment without utilizing an enzyme or other complicated compounds. Optionally, the reaction mixture is treated with water or steam to produce a reaction product before the step of analyzing the reaction product.

BRIEF DESCRIPTION OF THE DRAWINGS

FIG. 1 is a process step chart showing the first inventive analysis method.

FIGS. 6(A)–6(C) show various analysis results of reaction mixtures of another peptide analyzed by FAB-MS, where the nonapeptide of sample No. 2 is treated by vapors containing HFBA for 4 hours (FIG. 6(B)) and for 24 hours (FIG. 6(C)), and the nonapeptide is not treated by the organic acid (FIG. 6(A))

FIG. 12 is a process step chart showing the second inventive analysis method.

DETAILED DESCRIPTION OF THE INVENTION

Hereinafter, the first aspect of the present invention will be described in conjunction with Examples 1–6.

EXAMPLE 1

The first experimental method is described in this example. FIG. 1 is a process step chart showing the first inventive analysis method. A protein or peptide is treated by trifluoroacetic acid (TFA), pentafluoropropionic acid (PFPA) or heptafluorobutylic acid (HFBA) to cause successive degradation reaction from a C-terminal. The resulting reaction mixture is analyzed by a fast atom bombardment mass spectrometer (FAB-MS) or an electro-spray ionization mass spectrometer (ESI-MS) to obtain a mass spectrum, or the reaction mixture is processed by an amino acid analyzer.

Figure 2:
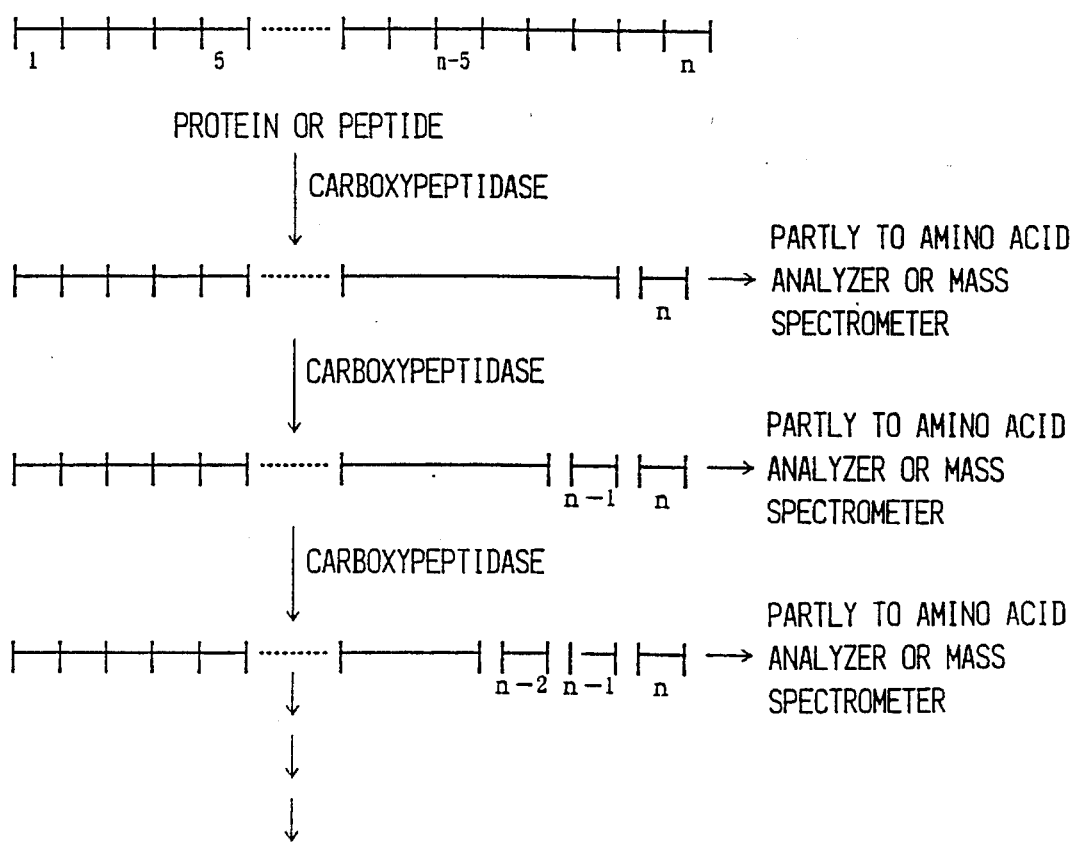
FIG. 2 is a process step chart showing one conventional analysis method utilizing carboxypeptidase.
Figure 3:
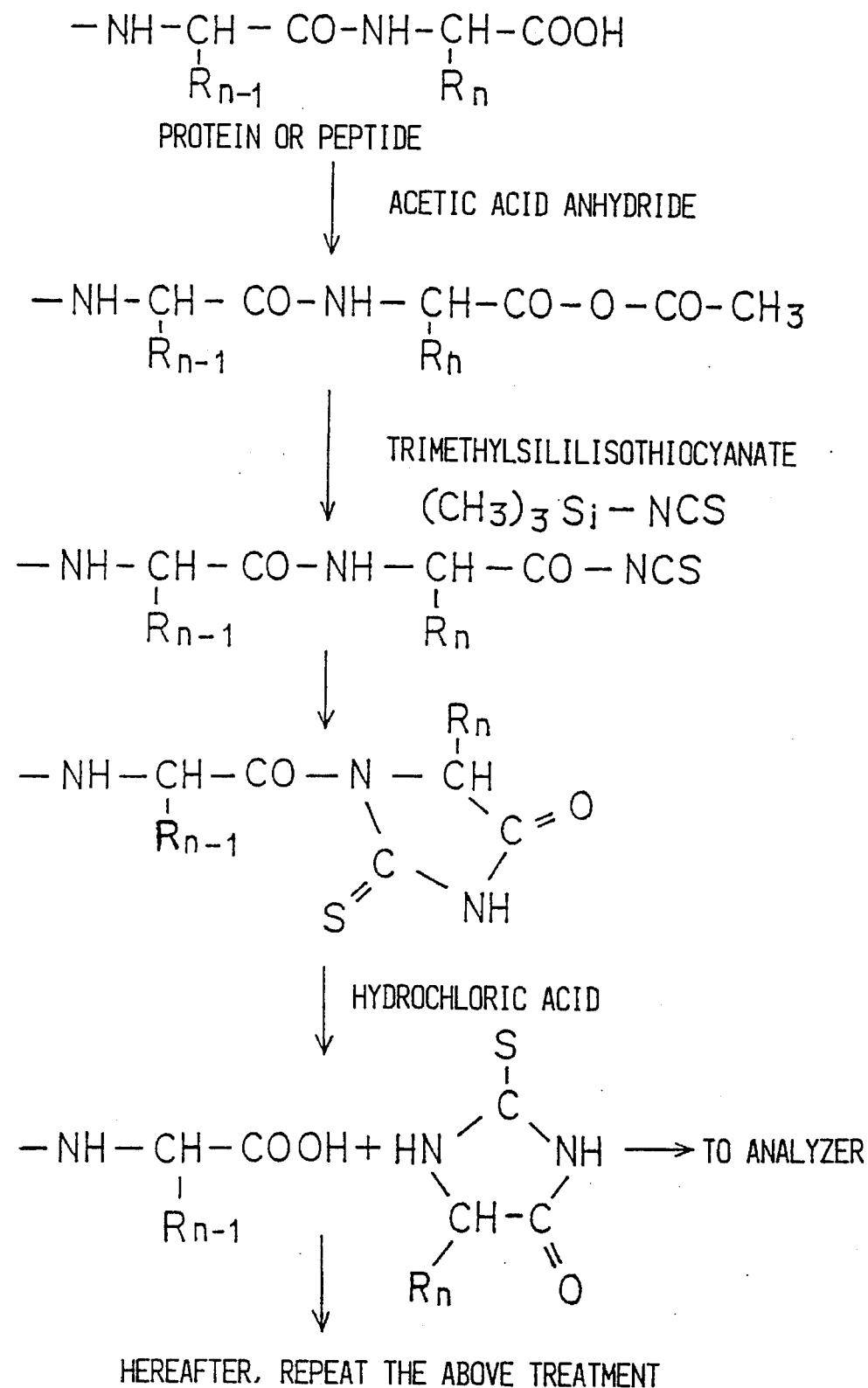
FIG. 3 is a process step chart showing another conventional analysis method utilizing trimethylsililisothiocyanate.
Figure 4A:
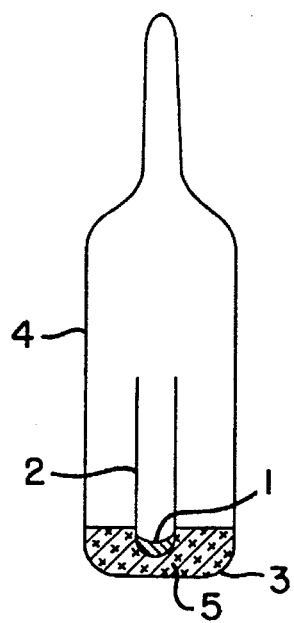
FIG. 4(A) shows an experimental system according to a first aspect of the invention, in which a reducing agent is added into an aqueous solution of an organic acid.
Figure 4B:
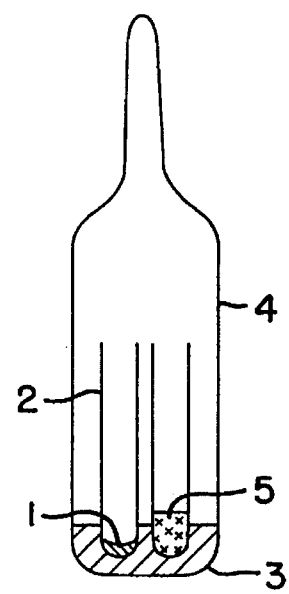
FIG. 4(B) shows another experimental system according to a first aspect of the invention, in which a reducing agent is charged into a small test tube which is different from another small test tube containing a protein or a peptide.

The analysis procedure of the invention is as follows. A sample solution 1 containing a protein or a peptide is charged into a small test tube 2 and is then dried. This small test tube 2 is placed in an outer test tube 4 which contains an aqueous solution 3 of TFA, PFPA or HFBA. In this stage, a reducing agent 5 is added in the aqueous solution (FIG. 4(A)). Alternatively, instead of adding the reducing agent into the aqueous solution of the organic acid, the reducing agent 5 may be placed in another separate small test tube, which is then placed together with the small test tube 2 containing the protein or peptide 1 in the outer test tube 4 containing the aqueous solution of the organic acid (FIG. 4(B)).

Next, the outer test tube is flame-sealed under a reduced gas pressure state. Then, the double structure of the test tubes is heated. Thereafter, the sealed outer tube is opened and the inner tube is taken out and dried. The dried sample is dissolved into an aqueous solution of acetic acid, and further the aqueous solution is added with a mixture of glycerol and thioglycerol. Thereafter, the sample is analyzed by FAB-MS. Alternatively, in case that the sample is analyzed by ESI-MS, the sample is dissolved into a methanol solution containing acetic acid, and then the sample is introduced into an ESI-MS device.

The condition of the mass spectrography is as follows:

FAB-MS

Mass spectrometer: model HX110 produced by Japan Electronics Co., Ltd.

Data processing system: DA1000 produced by Japan Electronics Co., Ltd.

Acceleration voltage: 10 KV

Ion gas species: xenon

ESI-MS

Mass spectrometer: SX-101 produced by Japan Electronics Co., Ltd.

Acceleration voltage: 10 KV

Ion gas species: nitrogen

Alternatively, in case that the amino acid analyzer is utilized for the analysis, the sample is dissolved into a citric acid butter solution of pH 2.2 and is then introduced into the analyzer. The utilized analyzer is a model A-5500 produced by Iricakiki Co., Ltd., which performs amino acid analysis by the ninhydrin method according to ion exchange chromatograph.

EXAMPLE 2

In order to demonstrate the invention, an experiment is conducted while selecting, as a sample peptide, hexapeptide of sample No. 1, Leu-Trp-Met-Arg-Phe-Ala. Hereinafter, for example, a segment Leu-Trp-Met is called "peptide 1-3". The various sample peptides are listed in the last part of the specification.

Figure 5D:
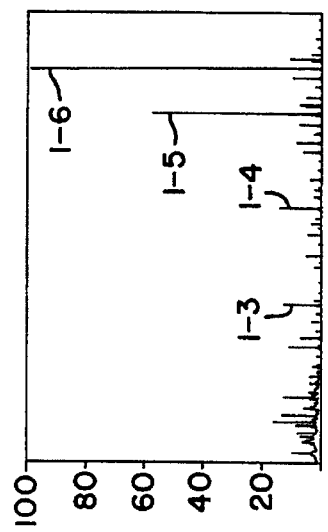
FIGS. 5(A)–5(F) show various analysis results of reaction mixtures of a peptide analyzed by FAB-MS, where the hexapeptide of sample No. 1 is treated by various vapors containing TFA (FIG. 5(B)), PFPA (FIG. (C)) and HFBA (FIG. 5(D)) for 4 hours, and where the hexapeptide is treated by PFPA (FIG. 5(E)) and HFBA (FIG. 5(F)) for 24 hours, and additionally, the hexapeptide is not treated by the organic acid (FIG. 5(A)).
Figure 5E:
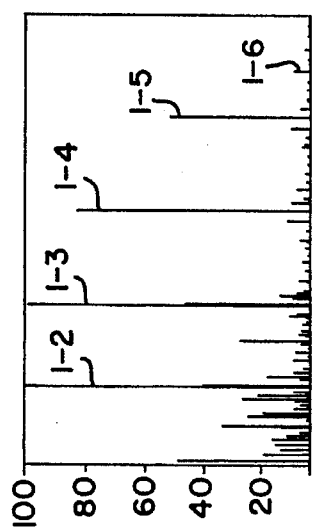
Figure 5F:
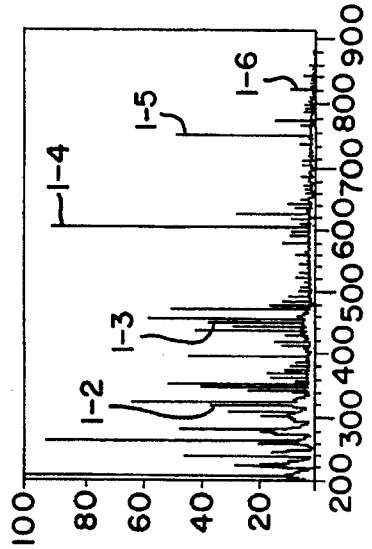
Figure 5A:
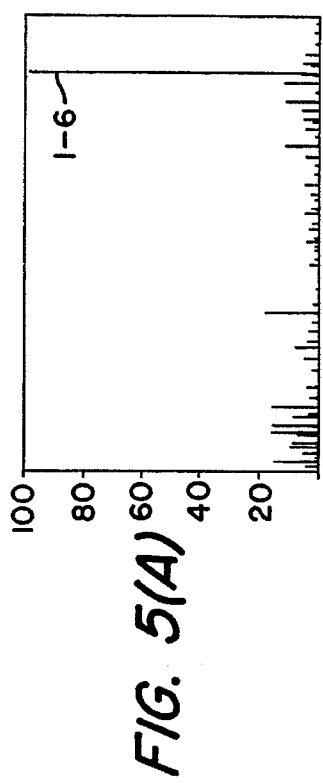
Figure 5B:
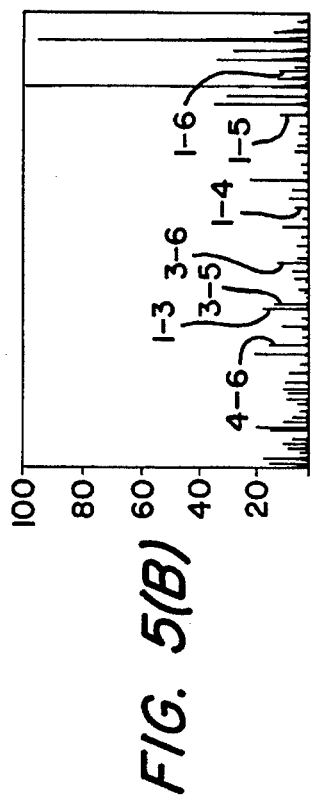
Figure 5C:
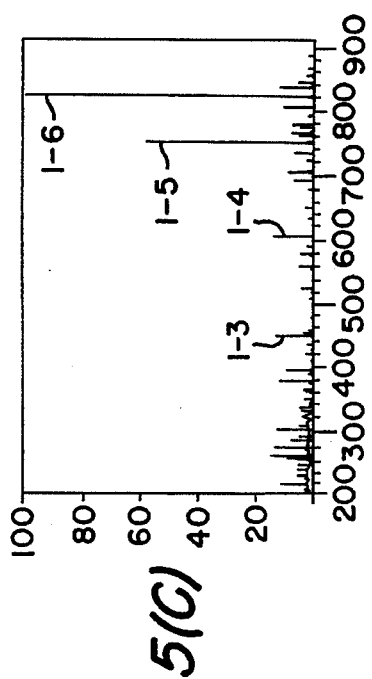

Results of the FAB-MS analysis are shown for the reaction mixture treated by acid vapors containing TFA (FIG. 5(B)), PFPA (FIGS. 5(C), 5(E)) or HFBA (FIGS. 5(D), 5(F)). In this experiment, the heating temperature is set to 90° C., and the concentration of the respective organic acid solution is set to 90%. FIG. 5(A) shows an analysis result of the peptide which is not subjected to the organic acid treatment. In case that the vapor containing TFA is applied to the sample for 4 hours, there is detected the whole peptide as well as degradated peptides 1-5, 1-4 and 1-3 which lack sequentially amino acids from the C-terminal. However, in this case, there are detected subsidiary peptides 4-6, 3-5 and 3-6 which are produced by nonspecific cleavage reaction within the peptide chain, rather than the sequential cleavage reaction from the C-terminal.

On the other hand, in case that either of PFPA (FIG. 5(C)) and HFBA (FIG. 5(D)) is applied to the sample for 4 hours, there are detected mainly the whole peptide 1-6 and fragmental peptides 1-5, 1-4 and 1-3 which are produced by sequential cleavages of the peptide chain from the C-terminal. It is understood that the amino acid sequence can be determined from the C-terminal based on the detection results.

Next, FIGS. 5(E) and 5(F) show the results obtained when the sample is treated for 24 hours by PFPA and HFBA, respectively. In these cases, there are detected cleaved peptides produced by sequential degradation of the peptide chain from the C-terminal in manner similar to the case where the sample is treated for 4 hours. However, there is detected additionally a fragmental peptide 1-2 which is not observed in case that the sample is treated for 4 hours. Thus, it is understood that a longer sequence of amino acids can be analyzed by applying the organic acid for a longer time period.

EXAMPLE 3

Further, the above described results are confirmed by using another peptide of sample No. 2, i.e., nonapeptide Arg-Val-Tyr-Ile-His-Pro-Phe-His-Leu. FIG. 6(A) shows an analysis result of the sample peptide which is not treated by the organic acid. FIG. 6(B) shows another analysis result in case that the sample is treated by 90% of HFBA for 4 hours at 90° C. The peptides 1-9, 1-8 and 1-7 are detected so that a sequence of the last two amino acid units from the C-terminal is determined or identified. In case that the sample is treated for 24 hours (FIG. 6(C)), there are detected peptides 1-9, 1-8, 1-7, 1-6, 1-5, 1-4 and 1-3 so that a sequence of the last six amino acid units is identified.

EXAMPLE 4

Figure 7A:
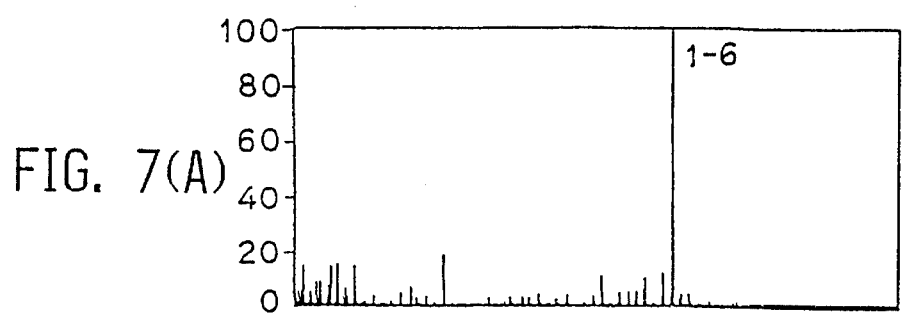
FIGS. 7(A)–7(E) show various analysis results of the hexapeptide of sample No. 1 treated by PFPA at 90° C. for 4 hours while varying the concentration of PFPA in the range of 50%–98%, where the concentration of PFPA is set to 50% (FIG. 7(B)), 70% (FIG. 7(C)), 90% (FIG. 7(D)) and 98% (FIG. 7(E)), and the hexapeptide is not treated by the organic acid (FIG. 7(A)).
Figure 7B:
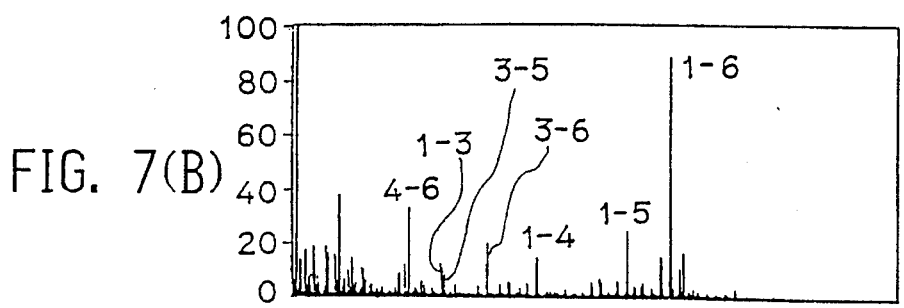
Figure 7C:
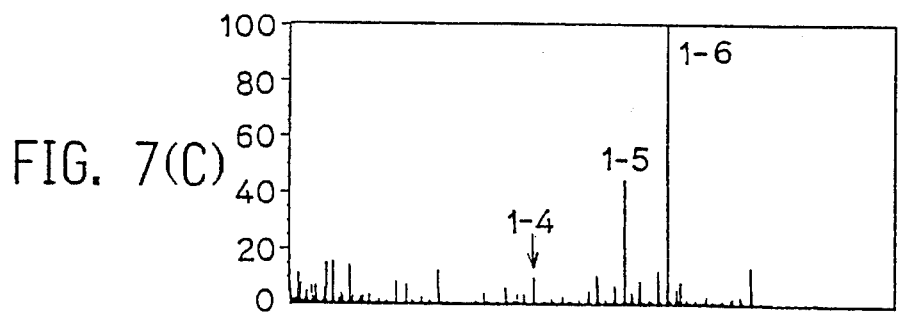
Figure 7D:
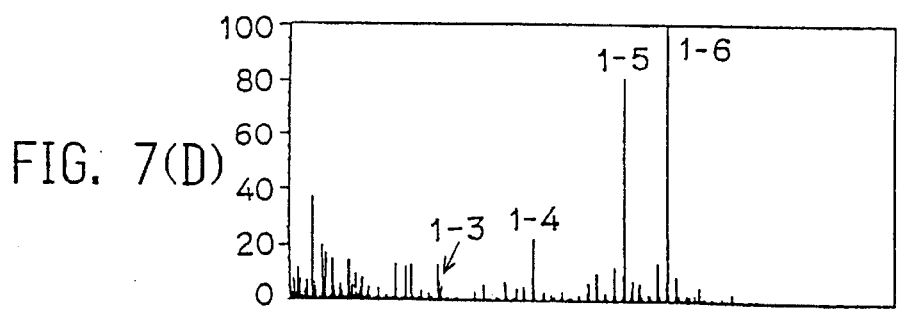
Figure 7E:
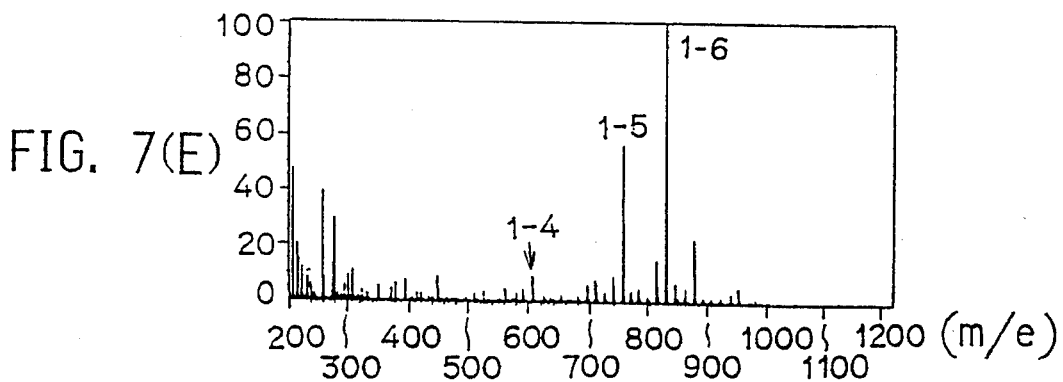

This example shows analysis results obtained when a sample is treated by variable concentrations of the organic acid. FIGS. 7(A)–7(E) show the detection results obtained by FAB-MS analysis of a reaction mixture which is obtained by applying PFPA having variable concentration in the range of 50%–98% to the sample for 4 hours at 90° C. The sample is hexapeptide of sample No. 1, Leu-Trp-Met-Arg-Phe-Ala. FIG. 7(A) shows an analysis result in case that the sample peptide is not treated by the organic acid. FIG. 7(B) shows another analysis result in case that the sample is treated by 50% of PFPA. In similar manner, FIGS. 7(C), 7(D) and 7(E) show different results in case that the concentration is set to 70%, 90% and 98%, respectively. In case that the concentration of PFPA is set to 50%, there are detected subsidiary peptide fragments 4-6, 3-5 and 3-6 produced by nonspecific dissociation reaction within the peptide chain, besides the sequential cleavage from the C-terminal. It is understood that the specific cleavage most efficiently occurs sequentially in the peptide chain from the C-terminal in case that the concentration of the organic acid is set to 90%.

Figure 8A:
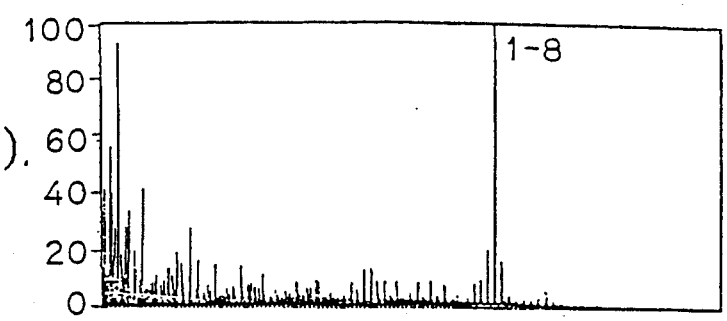
FIGS. 8(A)–8(E) show various analysis results of an octapeptide of sample No. 3 treated by HFBA at 90° C. for 4 hours while varying the concentration of HFBA in the range of 50%–98%, where the concentration of HFBA is set to 50% in FIG. 8(B), 70% in FIG. 8(C), 90% in FIG. 8(D) and 98% in FIG. 8(E), and the octapeptide is not treated by the organic acid in FIG. 8(A).
Figure 8B:
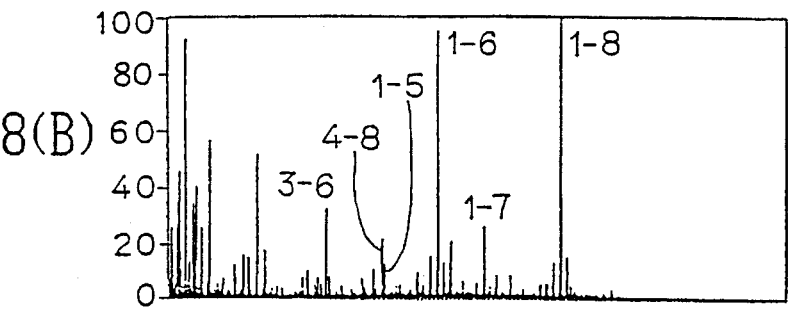
Figure 8C:
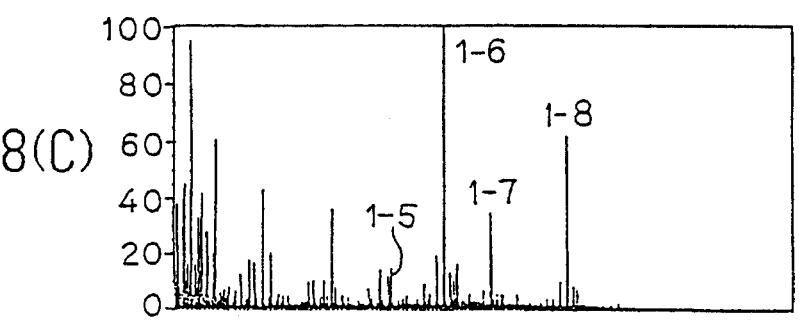
Figure 8D:
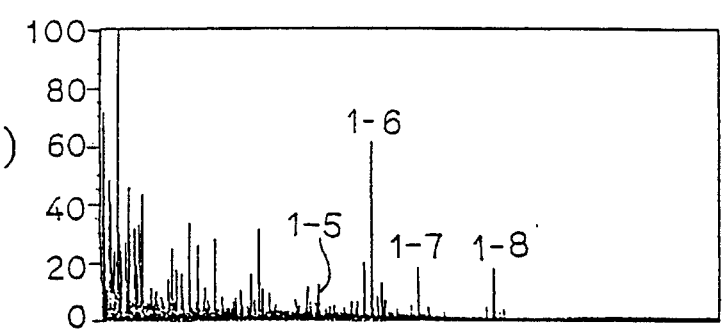
Figure 8E:
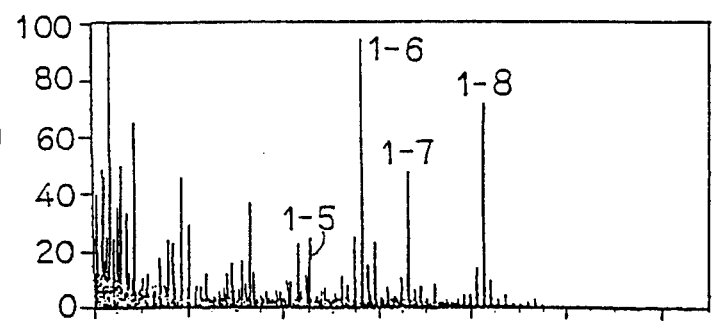

FIGS. 8(A)–8(E) show analysis results obtained in case that a sample is treated by HFBA for 4 hours at 90° C. while varying the concentration in the range from 50%–98%. The sample is octapeptide of sample No. 3, i.e., His-Pro-Phe-His-Leu-Leu-Val-Tyr. FIG. 8(A) shows an analysis result in case that the sample is not treated by the organic acid. FIG. 8(B) shows another result in case that the sample is treated by HFBA having a concentration of 50%. In similar manner, FIGS. 8(C), 8(D) and 8(E) show different results in case that the concentration is set to 70%, 90% and 98%, respectively.

In case that the concentration of HFBA is set to 50%, there are detected by-product peptides 4-8 and 3-6 which are produced by nonspecific dissociation reaction within the peptide chain, besides the sequential cleavage from the C-terminal, in manner similar to the case utilizing PFPA.

EXAMPLE 5

Figure 9:
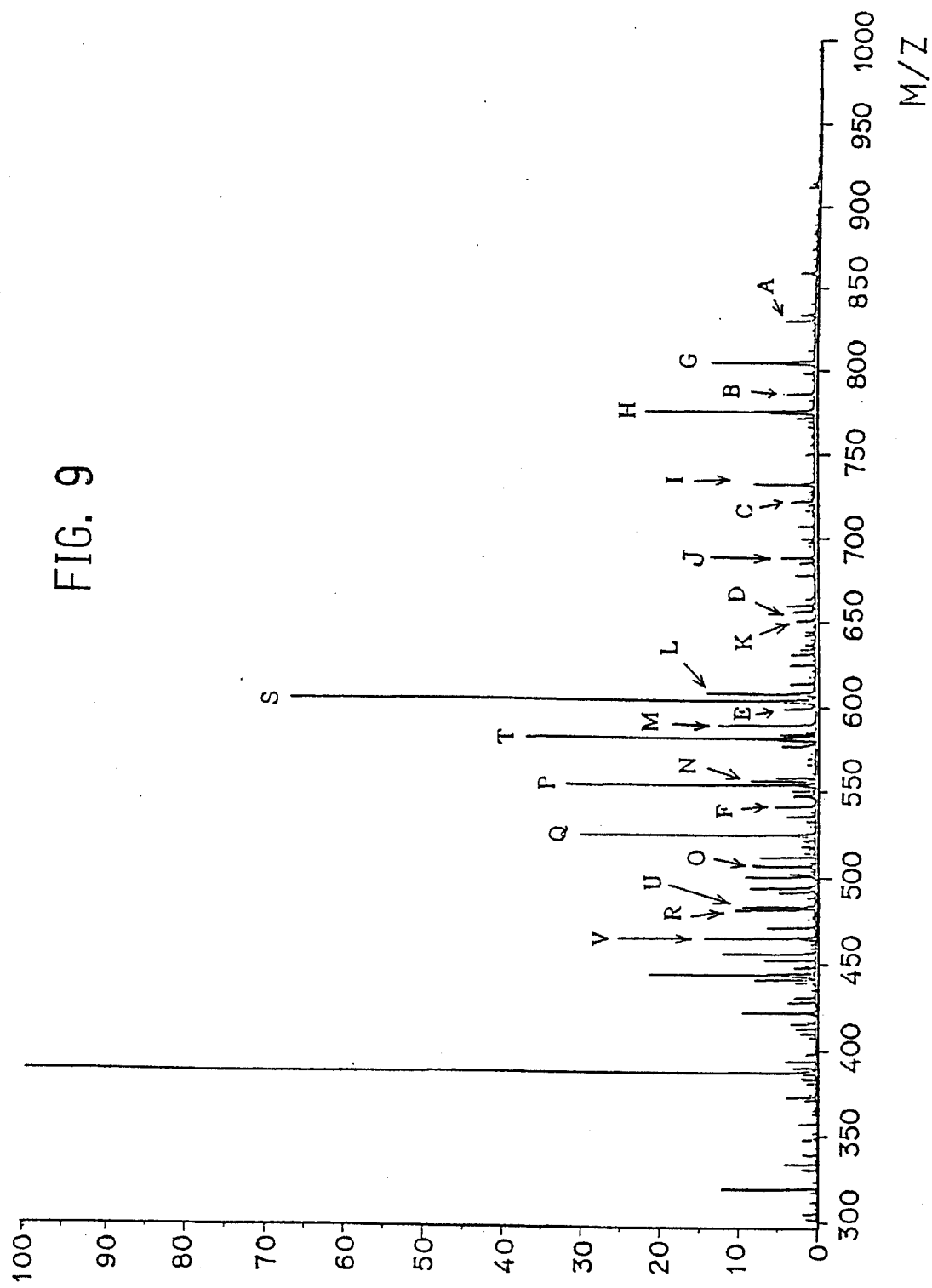
FIG. 9 shows a mass spectrogram indicating an analysis result in which ESI-MS is utilized to analyze a reaction mixture obtained by treating a tricosapeptide of sample No. 4 with PFPA for 2 hours.
Figure 10:
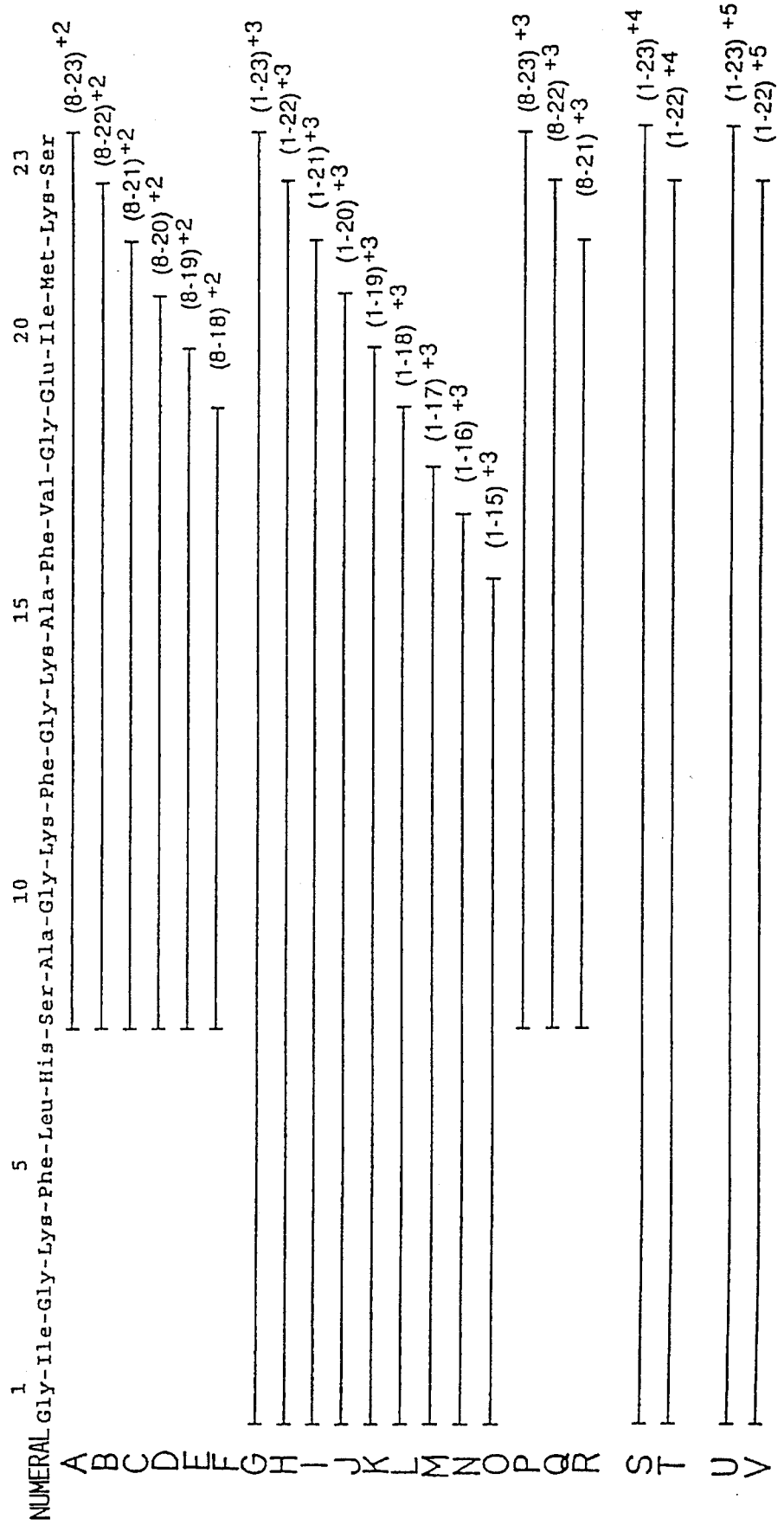
FIG. 10 is a diagram illustrating data of the FIG. 9 analysis results.

In this example, a reaction mixture is analyzed with using ESI-MS. FIGS. 9 and 10 show an analysis result, in which ESI-MS is utilized to analyze the reaction mixture which is obtained by applying 90% concentration of PFPA for 2 hours at 90° C. to tricosapeptide of sample No. 4, i.e., Gly-Ile-Gly-Lys-Phe-Leu-His-Ser-Ala-Gly-Lys-Phe-Gly-Lys-Ala-Phe-Val-Gly-Glu-Ile-Met-Lys-Ser. FIG. 9 is a mass spectrogram, and FIG. 10 is a diagram illustrating the data of the spectrongram. Each reference character in the FIG. 9 spectrogram corresponds to each reference character in FIG. 10. For example, a reference numeral $(8-23)2^+$ in FIG. 10 denotes an ionized peptide 8-23 having double positive charges. ESI-MS features that ions having various charge units are detected. In this case, ions having triple charges are selectively detected to determine a sequence of the last eight amino acid units from the C-terminal through the ions $(1-23)3^+$–$(1-15)3^+$.

EXAMPLE 6

Figure 11A:
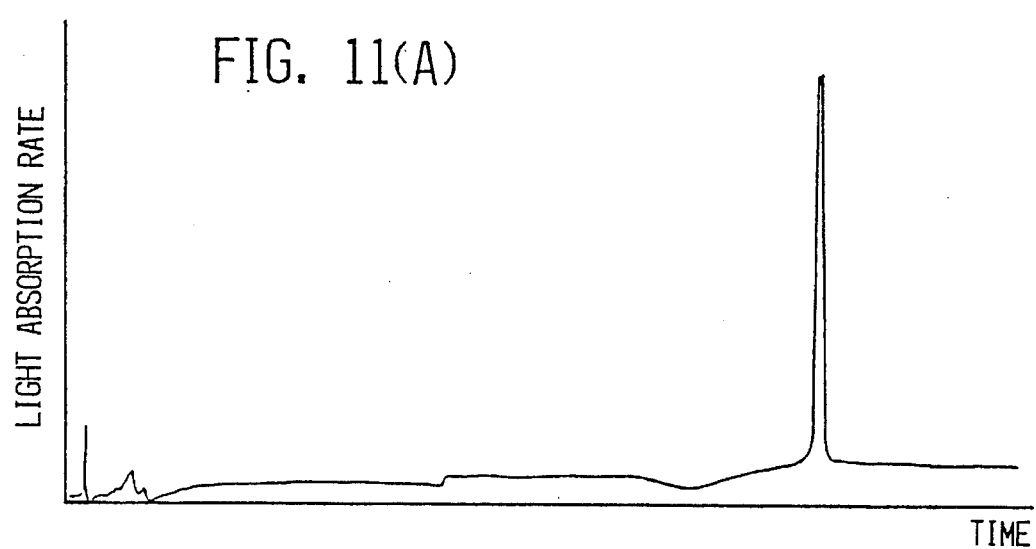
FIGS. 11(A)–11(C) show analysis results in which an amino acid analyzer is utilized to analyze reaction mixtures of the hexapeptide of sample No. 1 treated by a vapor containing PFPA for 4 hours (FIG. 11(B)) and 24 hours (FIG. 11(C)), and not treated by the organic acid in FIG. 11(A) case.
Figure 11B:
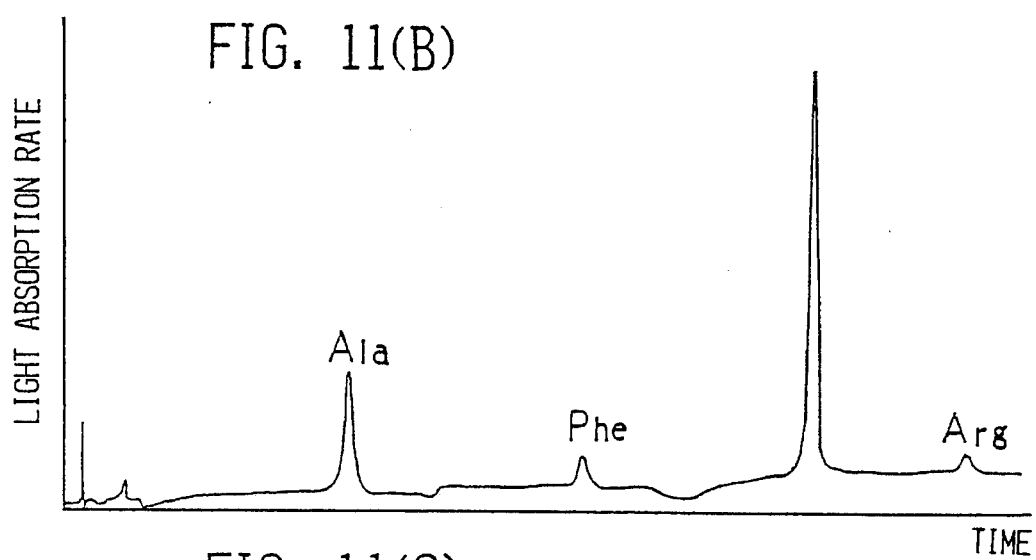
Figure 11C:
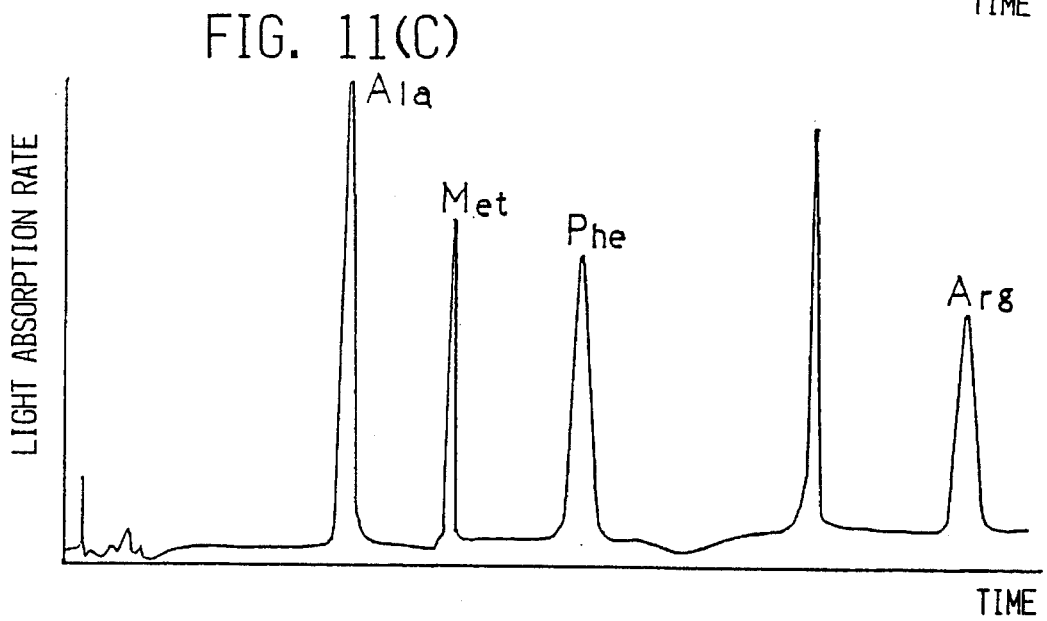

In this example, the amino acid analyzer is utilized to analyze a reaction mixture. FIGS. 11(B) and 11(C) show analysis results in case that the amino acid analyzer is utilized to analyze reaction mixtures which are obtained by applying a vapor containing PFPA for 4 hours and 24 hours, respectively, to hexapeptide of sample No. 1, i.e., Leu-Trp-Met-Arg-Phe-Ala, in manner similar to the Example 2. The remaining reaction conditions are also set in manner similar to the Example 2 such that heating temperature is set to 90° C., and the concentration of the organic acid is set to 90%. FIG. 11(A) shows an analysis result in case that the sample is not treated by the organic acid. According to a sequence of respective amino acid peaks shown in FIG. 11(B), it is determined that the sample has an amino acid sequence of -Arg-Phe-Ala from the C-terminal. Further, according to another sequence of respective amino acid peaks shown in FIG. 11(C), it is determined that the sample has an amino acid sequence of -Met-Arg-Phe-Ala from the C-terminal.

The above described Examples 1–6 are summarized as follows. The dried peptide is treated by a vapor which is produced by vaporizing an aqueous solution containing 50–98% of the organic acid represented by the general formula $CF_3-(CF_2)n-COOH$ (n is zero or more integer) and a reducing agent. The resulting reaction mixture is processed by FAB-MS or ESI-MS obtain a mass spectrum indicative of the whole peptide of the sample and fragmented peptides produced by sequential degradation reaction of amino acids from the C-terminal of the sample peptide. The spectrum is analyzed to determine the amino acid sequence of the sample peptide from the C-terminal. Alternatively, the reaction mixture is processed by an amino acid analyzer to obtain peak data, which is analyzed to determine the amino acid sequence of the sample peptide from the C-terminal.

The first aspect of the present invention features that protein or peptide is treated by a specific organic acid represented by the general formula $CF_3-(CF_2)n-COOH$ (n is zero or more integer) such as trifluoroacetic acid (n=0), pentafluoropropionic acid (n=1) or heptafluorobutylic acid (n=2). By such treatment, the amino acid sequence can be determined from the C-terminal of the protein or peptide by simplified processing without using an enzyme.

Hereinafter, the second aspect of the present invention will be described in conjunction with Examples 7–11.

EXAMPLE 7

The second experimental method is described in this example. FIG. 12 is a process step chart showing the second inventive analysis method. A protein or peptide is treated by an anhydride of trifluoroacetic acid (TFA), pentafluoropropionic acid (PFPA) or heptafluorobutylic acid (HFBA) to cause successive degradation reaction form a C-terminal. The resulting reaction mixture is treated by water and thereafter analyzed by the fast atom bombardment mass spectrometer to obtain a mass spectrum.

Figure 13:
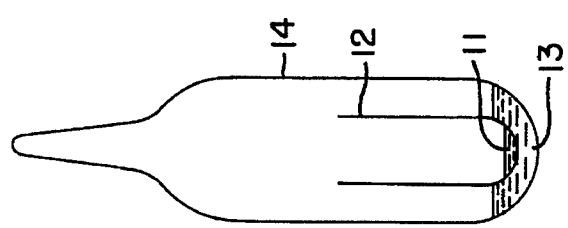
FIG. 13 is a diagram showing a sealing state of a sample utilized in the second inventive analysis.

The analysis procedure of the invention is as follows. Namely, a sample solution 11 containing a protein or a peptide is charged into a small test tube 12, and is then dried. This small test tube is placed in an outer large test tube 14 which contains an acetonitrile solution 13 of an anhydride of TFA, PFPA or HFBA. In this example, the concentration of the anhydride is set to 10%. In this arrangement, the sample solution 11 is not contacted with the anhydride solution 13 of the organic acid. Then, the outer test tube 14 is sealed under vacuum at a temperature of −30° C. This tube is stored at −18° C., as shown in FIG. 13. Thereafter, the sealed tube is opened, and a content is dried in vacuo. The dried sample is treated by a vapor of a water containing a pyridine under a weak alkaline condition. Thereafter, the treated sample is dissolved into a dimethyl formamide solution and is mixed with a glycerol, for analysis by FAB-MS. In this process, the second aqueous processing treatment is not inevitable but is optional.

The condition of mass spectrography is as follows:

FAB-MS

Equipment: Model HX110 produced by Japan Electronics Co., Ltd.

Ionization method: FAB (positive)

Ionization gas: xenon

Acceleration voltage: 10 KV

Matrix: glycerol

EXAMPLE 8

In order to demonstrate the present invention, this example is designed such that an experiment is undertaken while selecting, as a sample peptide, an octapeptide of sample No. 5, i.e., Lys-Lys-Lys-His-Pro-Asp-Tyr-Ile. In the following description, for example, a fragmental peptide Lys-Lys-Lys-His is denoted by a peptide 1-4.

Figure 14:
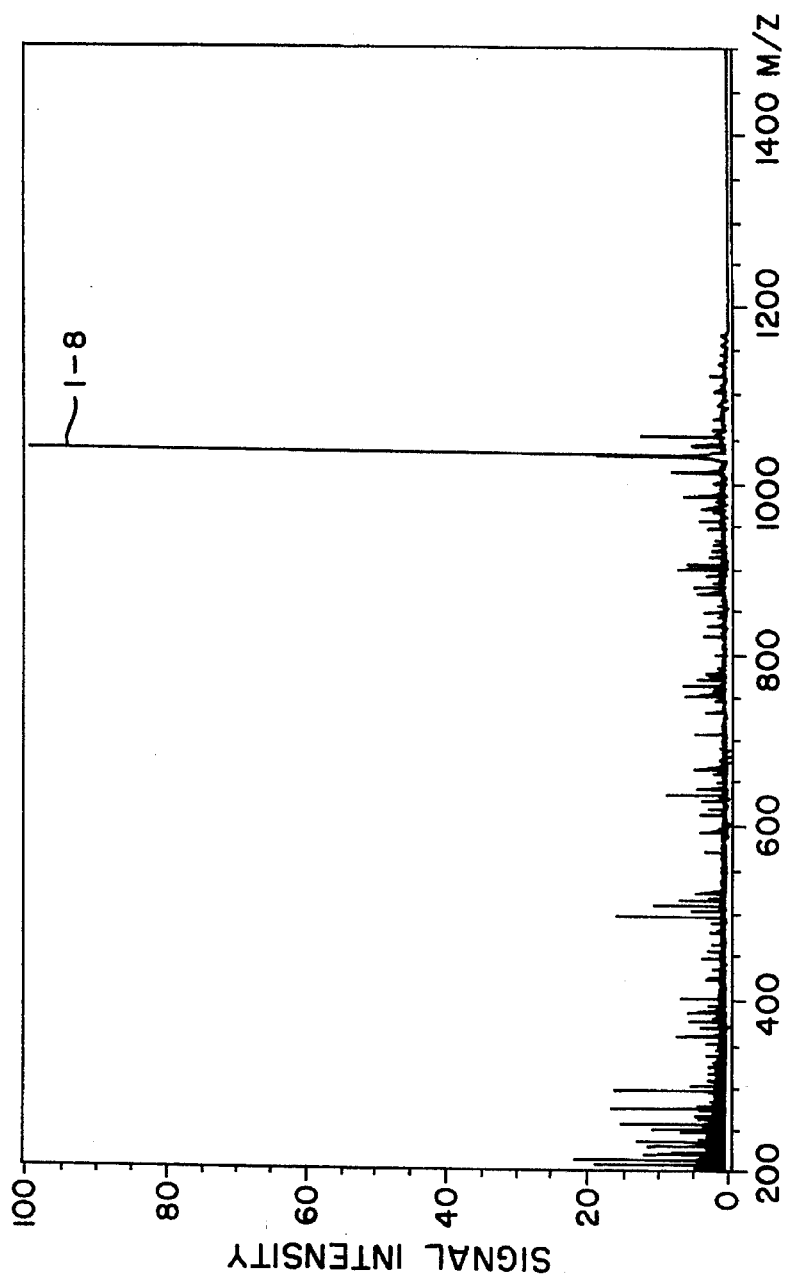
FIG. 14 is a diagram showing an analysis result of a sample peptide of sample No. 5 which is not treated by an acid anhydride.
Figure 15:
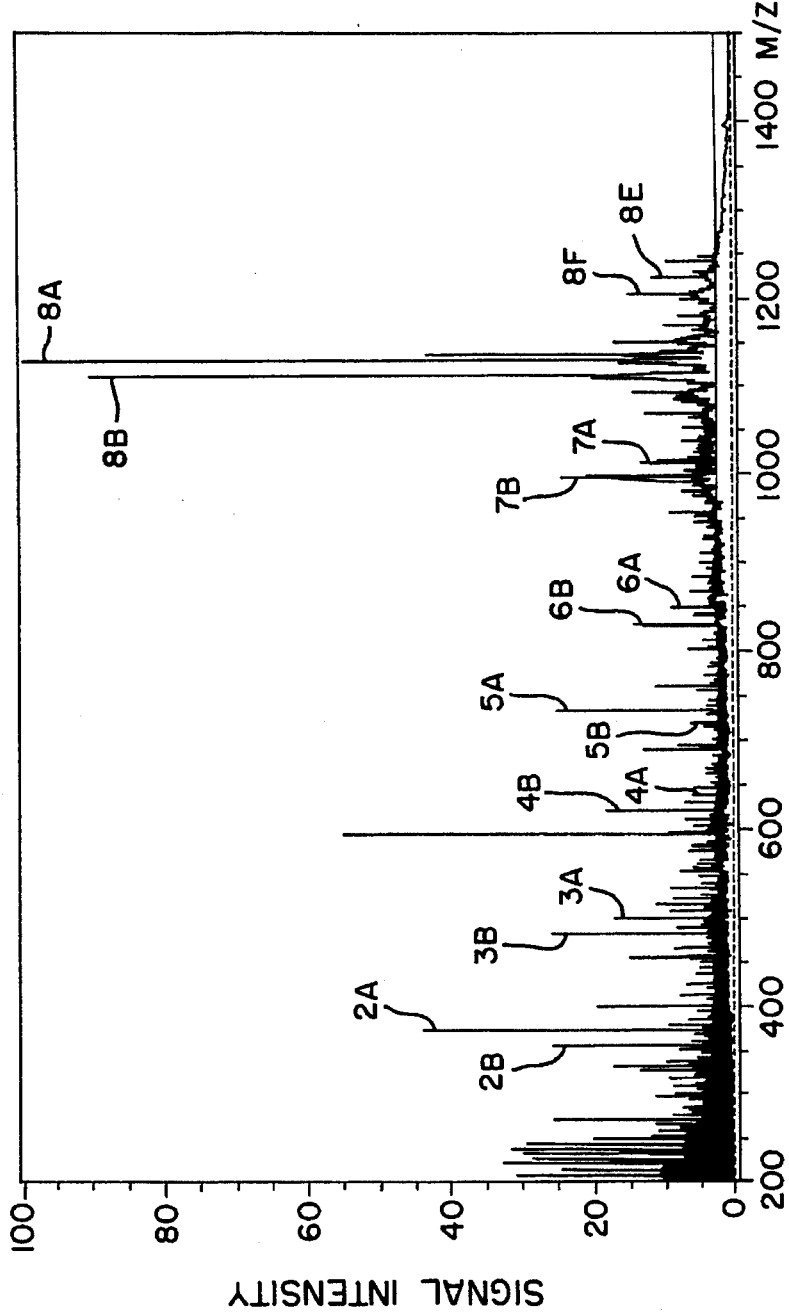
FIG. 15 is a diagram showing an analysis result of a reaction mixture of sample No. 5 treated by the anhydride of PFPA.
Figure 16:
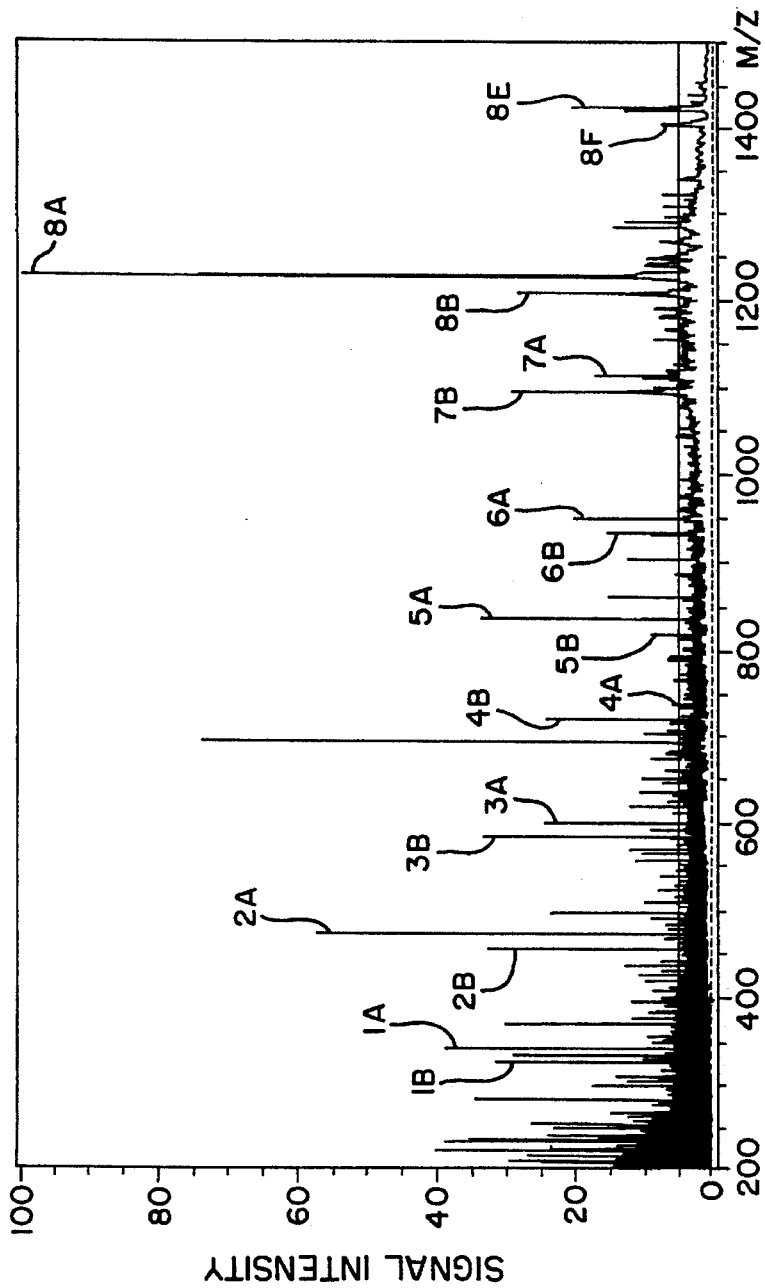
FIG. 16 is a diagram showing an analysis result of a reaction mixture treated by the anhydride of HFBA.
Figure 17:
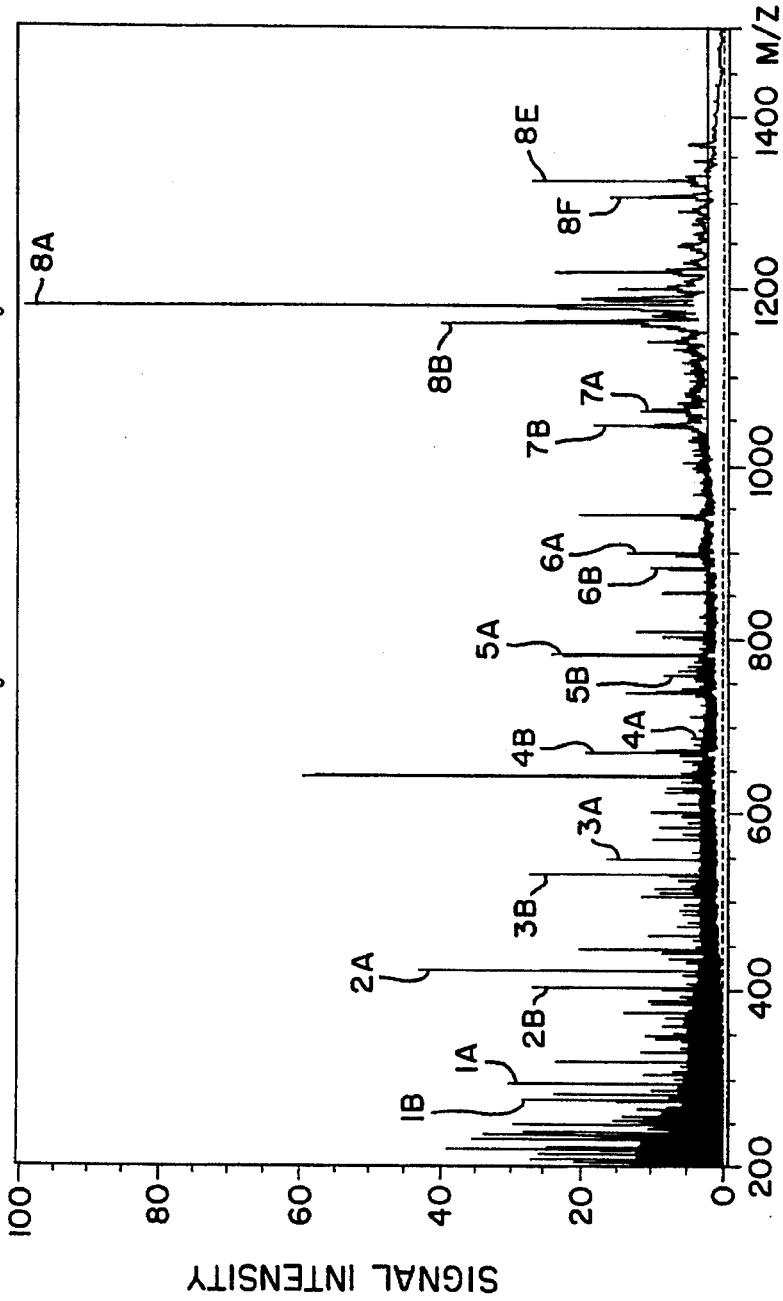
FIG. 17 is a diagram showing an analysis result of a reaction mixture treated by the anhydride of TFA.

FIGS. 15, 16 and 17 show analysis results obtained by using FAB-MS to analyze reaction mixtures produced by applying anhydrides of TFA, PFPA and HFBA, respectively. In this experiment, the concentration of the applied organic acid anhydrides is set to 10%, and the respective anhydrides are applied for 2 hours at −18° C. FIG. 14 shows an analysis result of the peptide of sample No. 5 which is not treated by an anhydride of the organic acid, for the comparison purpose.

FIG. 15 shows that the sequence analysis can be achieved from the C-terminal when the anhydride of TFA is applied. There are detected degraded peptides 1-8, 1-7, 1-6, 1-5, 1-4, 1-3 and 1-2 effective to thereby determine the sequence of the last six amino acid units from the C-terminal. In this example, the respective detected peptide is coupled with TFA and therefore is acylated. For example, an acylated peptide 1-8 is denoted by 1-8+Acyl. Further, there are observed peaks which correspond to products of degraded peptides losing one molecule of water as indicated by "$-H_2O$".

As understood from FIG. 16, in case that the anhydride of PFPA is applied, there are observed resulting peptides 1-8, 1-7, 1-6, 1-5, 1-4, 1-3 and 1-2 coupled to PFPA and an amino acid unit of the terminal (hereinafter, referred to as "1+Acyl"), thereby determining the complete amino acid sequence from the C-terminal. At the same time, there are detected a peptide 1-8 coupled with two molecules of PFPA (in similar manner, referred to as "1-8+diAcyl), and various degraded peptides which lose one molecule of water.

In similar manner, the FIG. 17 results show that the sequence analysis can be effected from the C-terminal by applying the anhydride of HFBA. There are detected peptides 1-8, 1-7, 1-6, 1-5, 1-4, 1-3, 1-2 and an amino acid unit of the terminal, those of which are coupled with HFBA, thereby determining the complete amino acid sequence from the C-terminal. At this time, there is detected concurrently a peptide 1-8 coupled with two molecules of HFBA. Further in similar manner, there are detected products of cleaved peptides which lose one molecule of water.

In any cases of the above noted example, there is not detected a subsidiary peptide which would be produced by cleavage of a peptide bond within the peptide chain. Therefore, analysis of peak data is facilitated for the determination of the amino acid sequence.

As described above, a protein or a peptide is treated by an anhydride of the specific organic acids represented by the general formula $CF_3-(CF_2)n-COOH$ (n is zero or more integer). The reaction products are processed by a mass spectrometer to obtain a mass spectrum. By measuring a mass of the respective products, the amino acid sequence can be determined from the carboxy-terminal of the protein or peptide.

EXAMPLE 9

Figure 18:
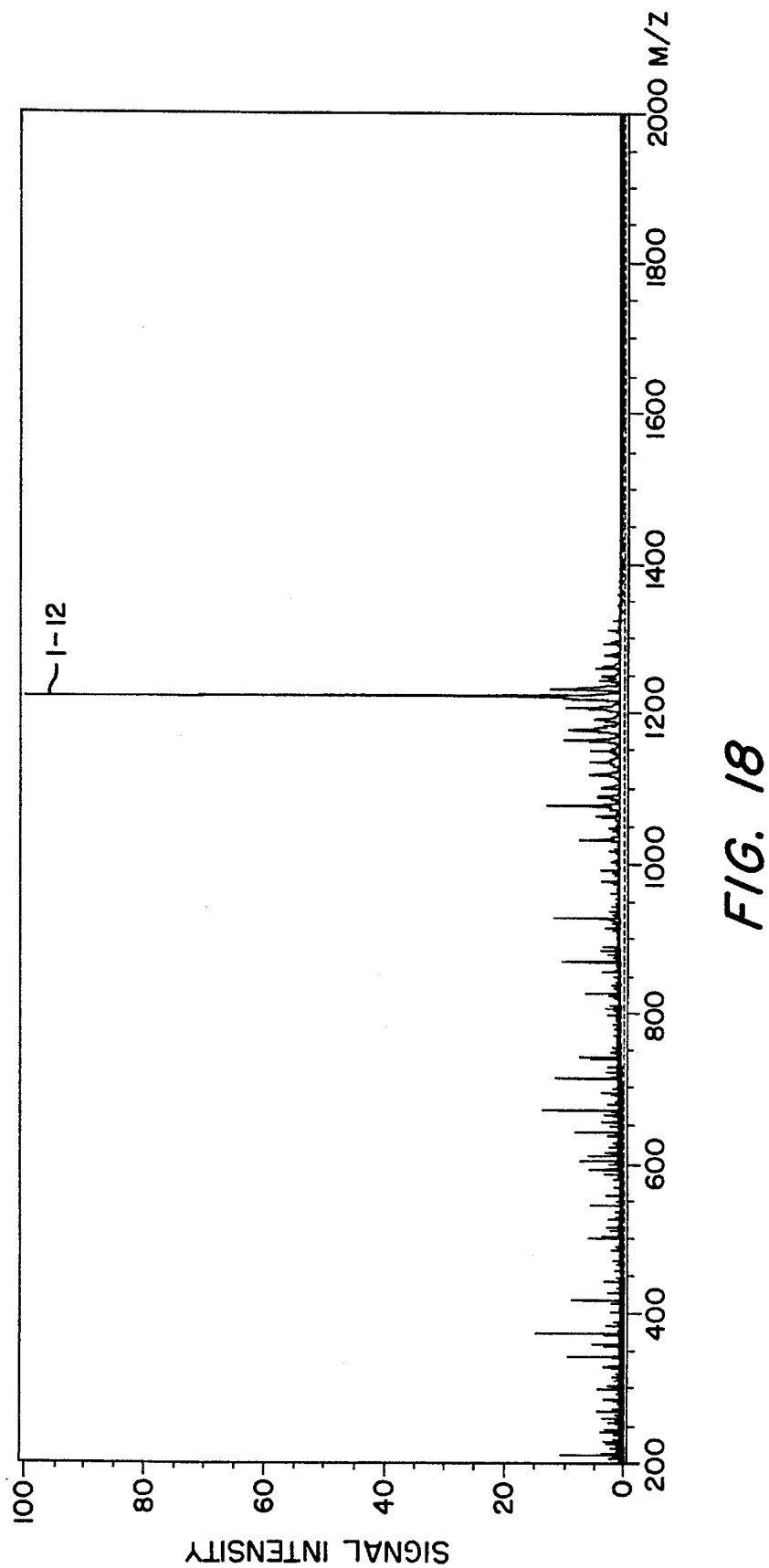
FIG. 18 is a diagram showing an analysis result of a sample peptide of sample No. 6 which is not treated by the anhydride of an acid.
Figure 19:
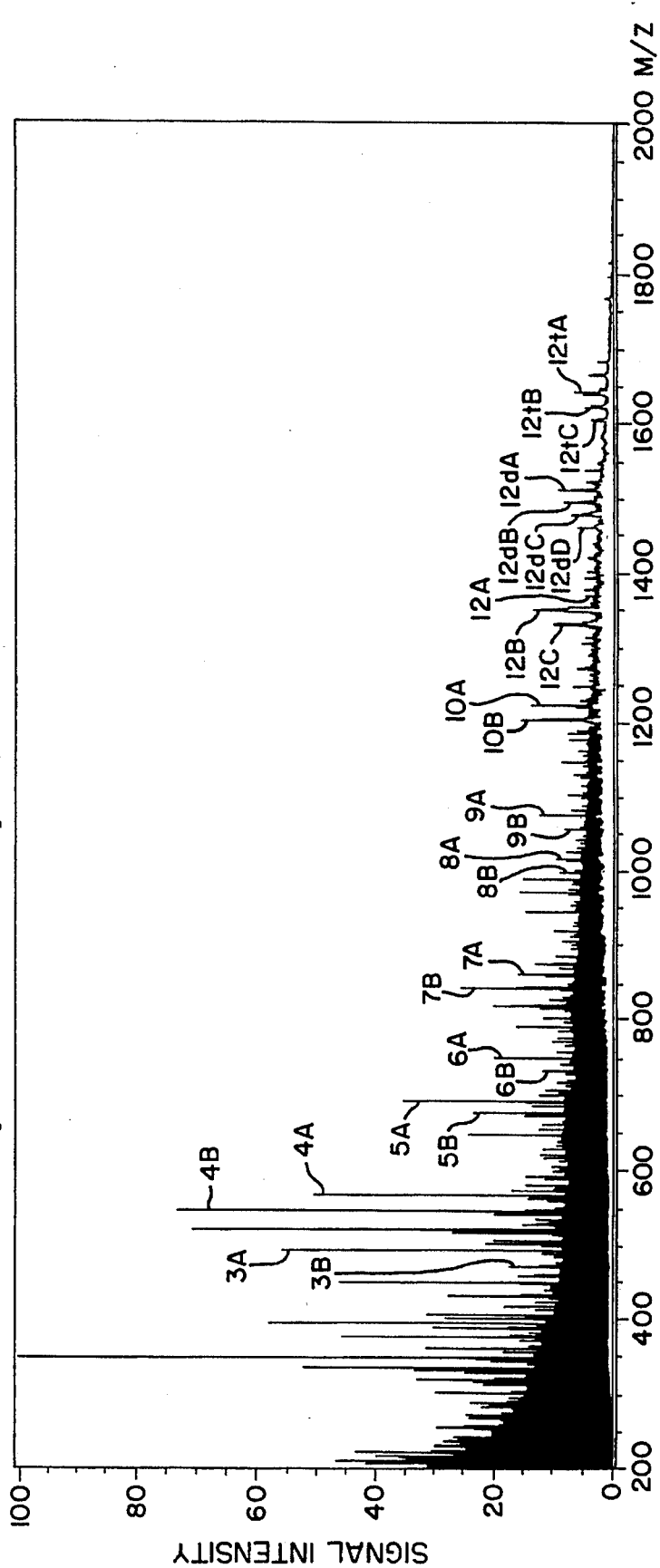
FIG. 19 is a diagram showing an analysis result of a reaction mixture of sample No. 6 which is treated by an acid anhydride for two hours at −18° C.
Figure 20:
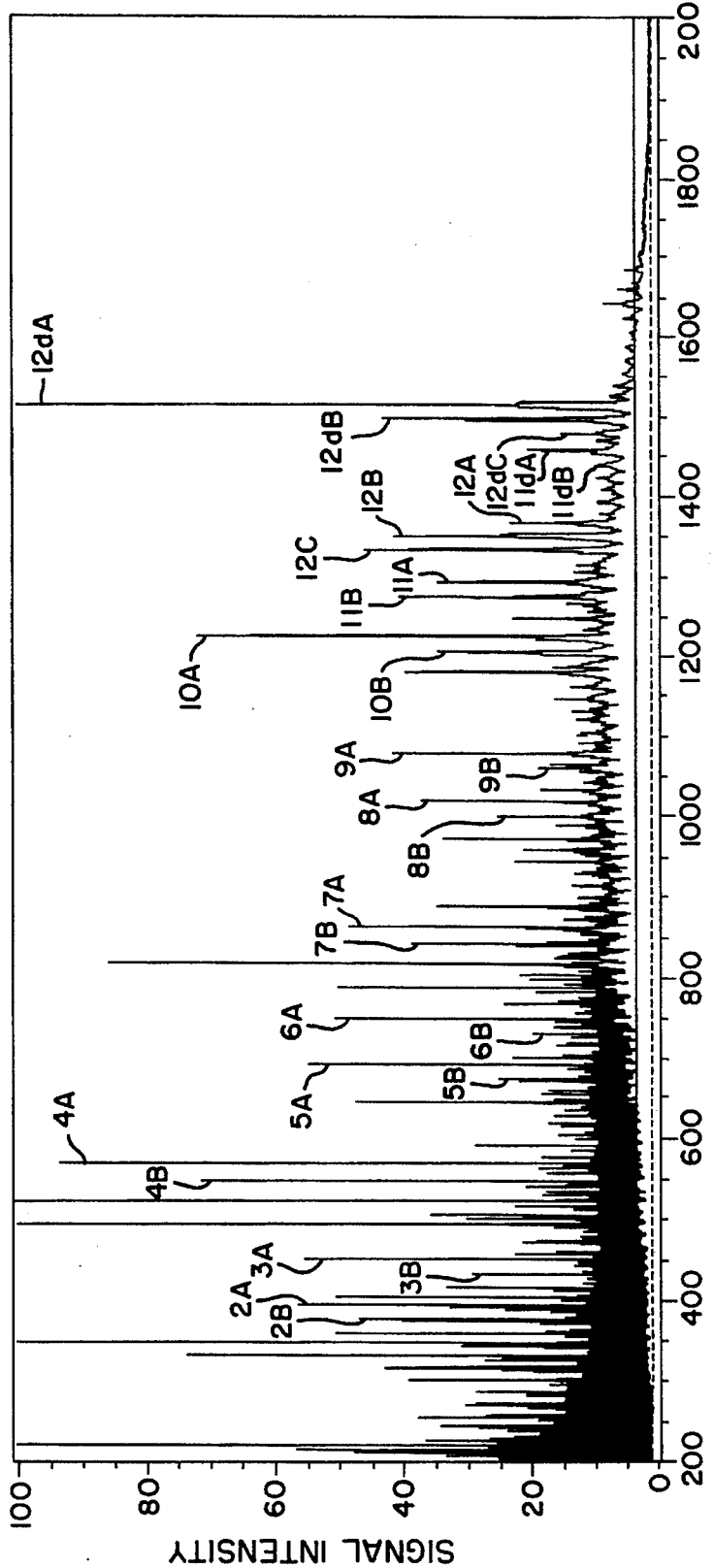
FIG. 20 is a diagram showing an analysis result of a reaction mixture which is treated by an acid anhydride for two hours at 0° C.

Next, there is examined an effect of the reaction temperature when the anhydride of the organic acid is applied, for the determination of the amino acid sequence. This example utilized a dodecapeptide of sample No. 6, Ala-Arg-Gly-Ile-Lys-Gly-Ile-Arg-Gly-Phe-Ser-Gly, which is treated by the anhydride of PFPA. FIGS. 19 and 20 show results obtained by processing, with a mass spectrometer, reaction mixtures treated by the anhydride of PFPA for two hours at temperatures −18° C. and 0° C., respectively. FIG. 18 shows an analysis result of the peptide of sample No. 6, which is not treated by the anhydride of the organic acid for the comparison purpose.

An shown in the results of FIGS. 19 and 20, there are detected peptides 1-12, 1-11, 1-10, 1-9, 1-8, 1-7, 1-6, 1-5, 1-4, 1-3 and 1-2 coupled with PFPA under the respective reaction conditions. It is understood that the sequence of the last ten amino acid units can be determined from the C-terminal under these conditions. At the same time, there is detected a peptide 1-12 coupled with two molecules of PFPA.

Further as shown in FIG. 20, there is detected a peptide 1-11 coupled with two molecules of PFPA in case that the anhydride of PFPA is applied for two hours at 0° C. Moreover in this case, there are detected more peaks which cannot be identified. It is understood from these results that a number of signals associated to by-products can be reduced while a relative signal intensity related to the objective reaction products can be increased, when the sample is treated at a lower temperature.

EXAMPLE 10

Figure 22:
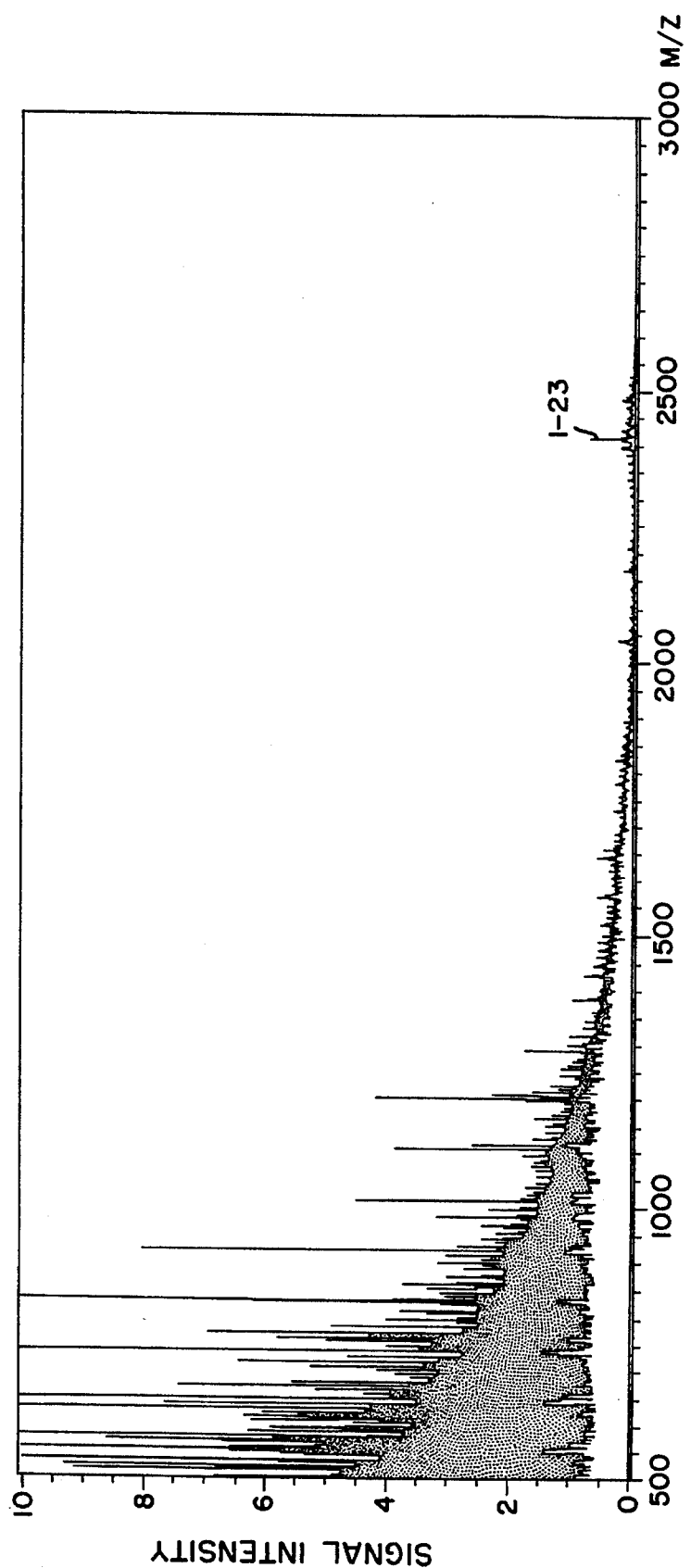
FIG. 22 is a diagram showing an analysis result of a peptide of sample No. 4 which is not treated by an acid anhydride.
Figure 23:
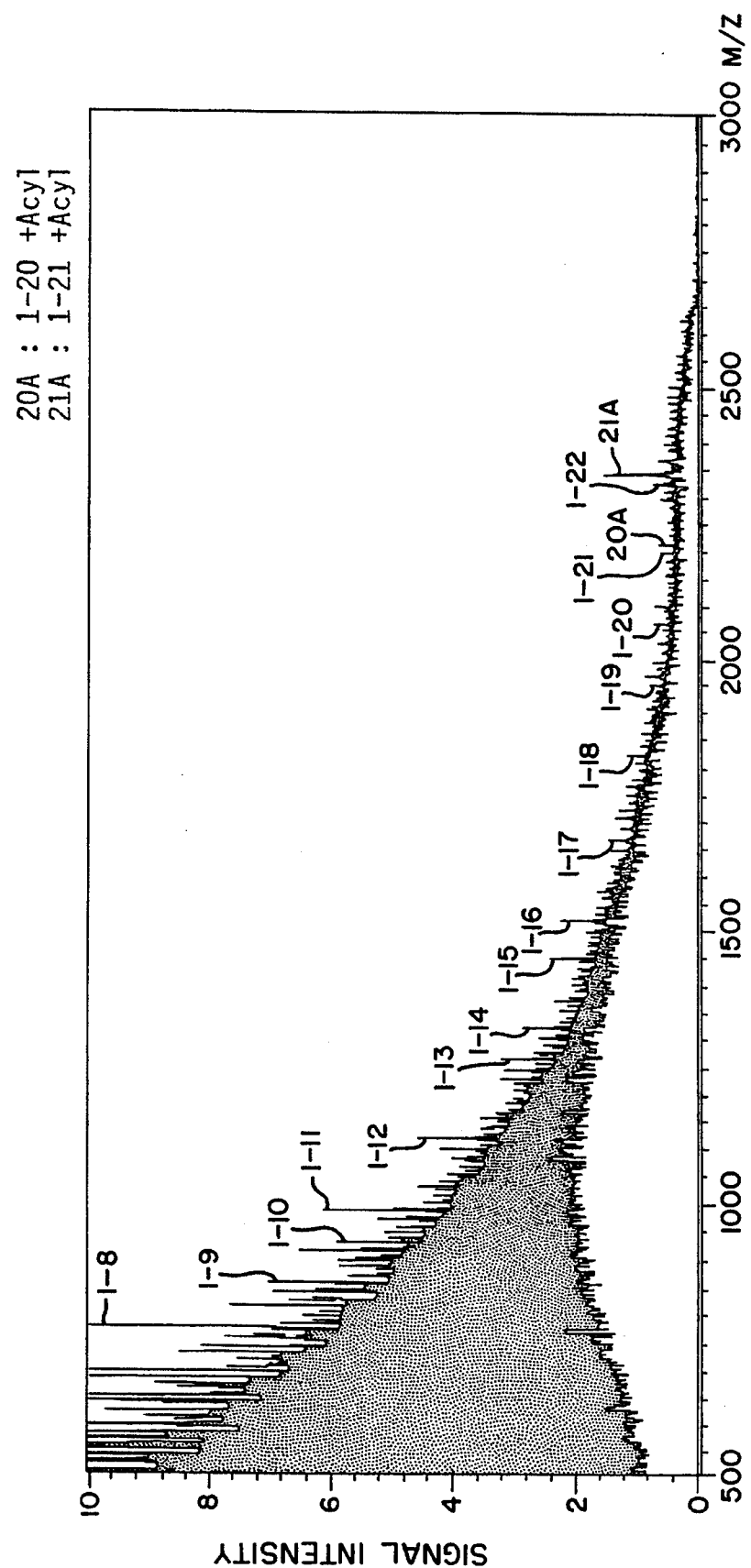
FIG. 23 is a diagram showing an analysis result of a reaction mixture of sample No. 4 which is treated by an acid anhydride for ten minutes at −18° C.
Figure 24:
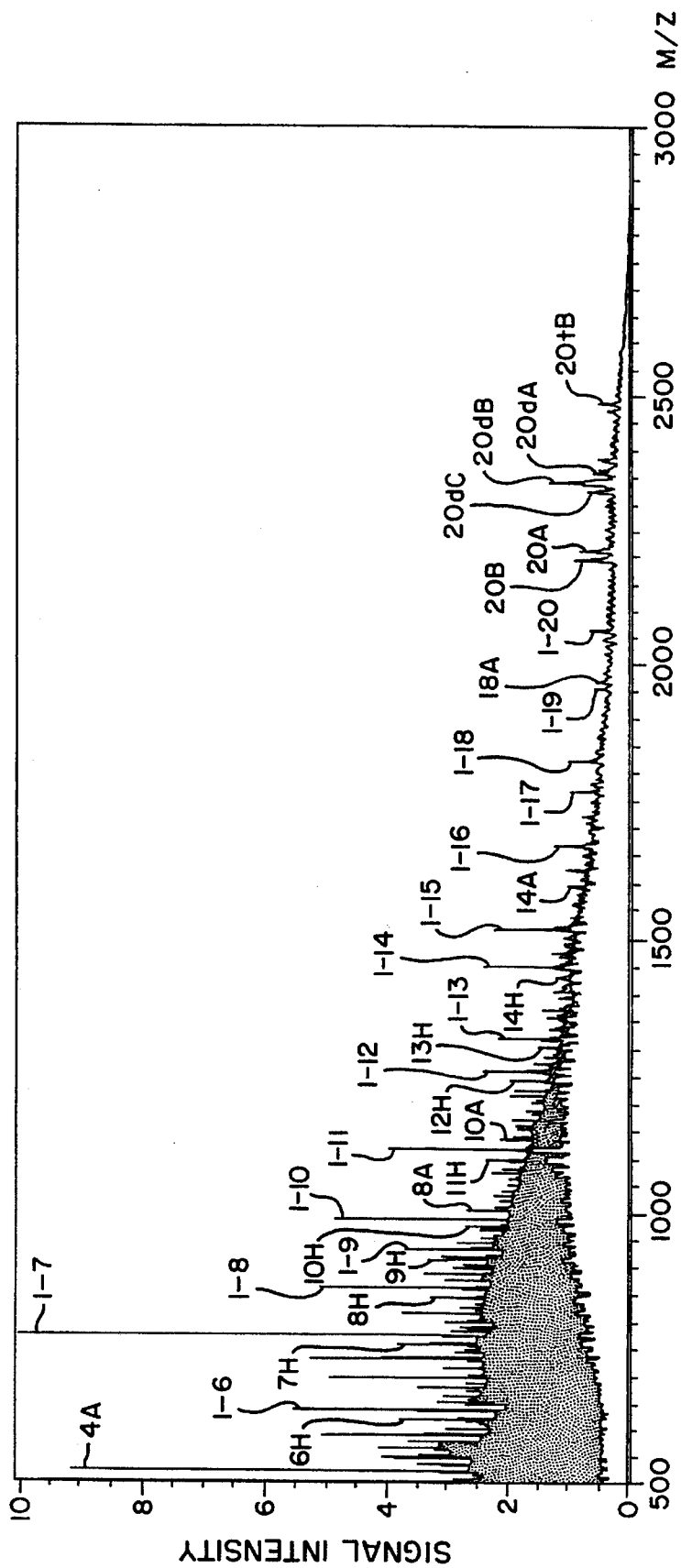
FIG. 24 is a diagram showing an analysis result of a reaction mixture which is treated by an acid anhydride for 30 minutes at −18° C.
Figure 25:
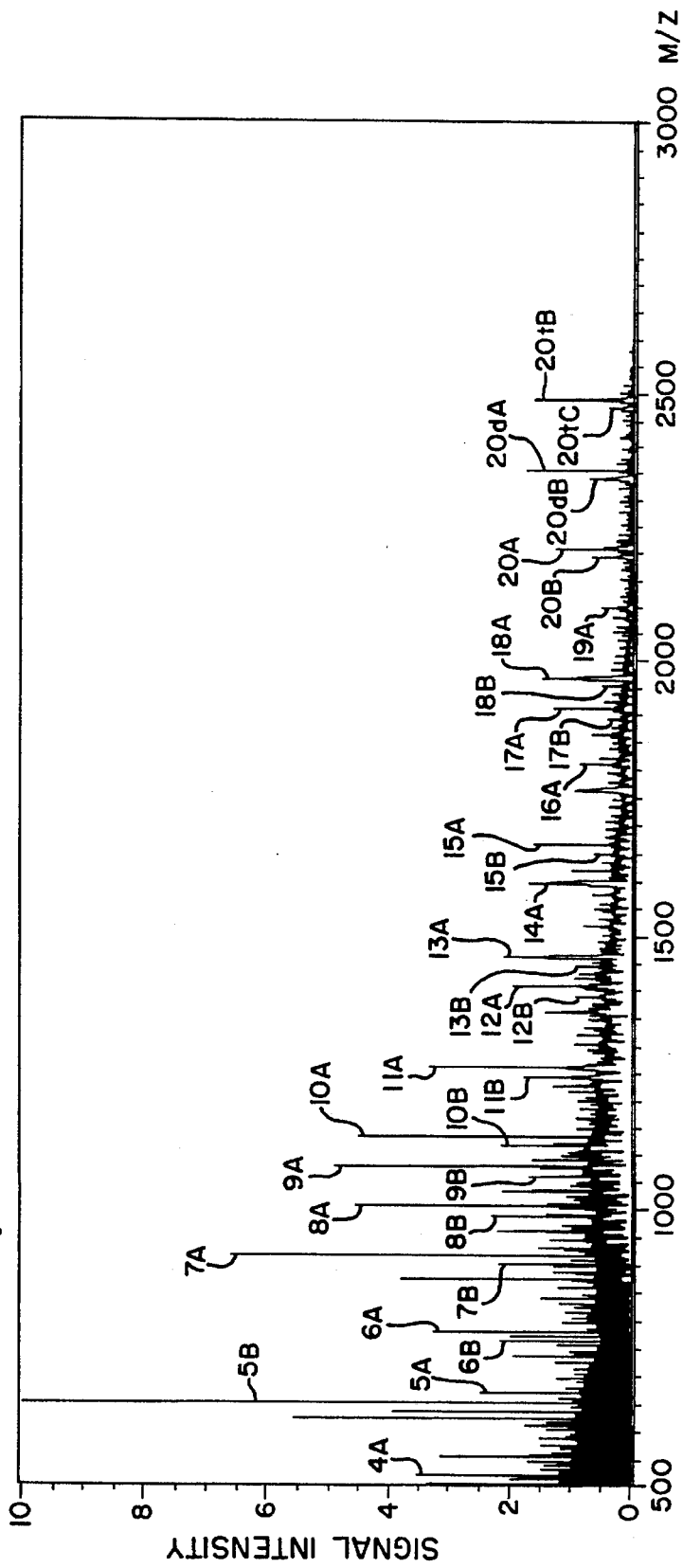
FIG. 25 is a diagram showing an analysis result of a reaction mixture which is treated by an acid anhydride for one hour at −18° C.
Figure 26:
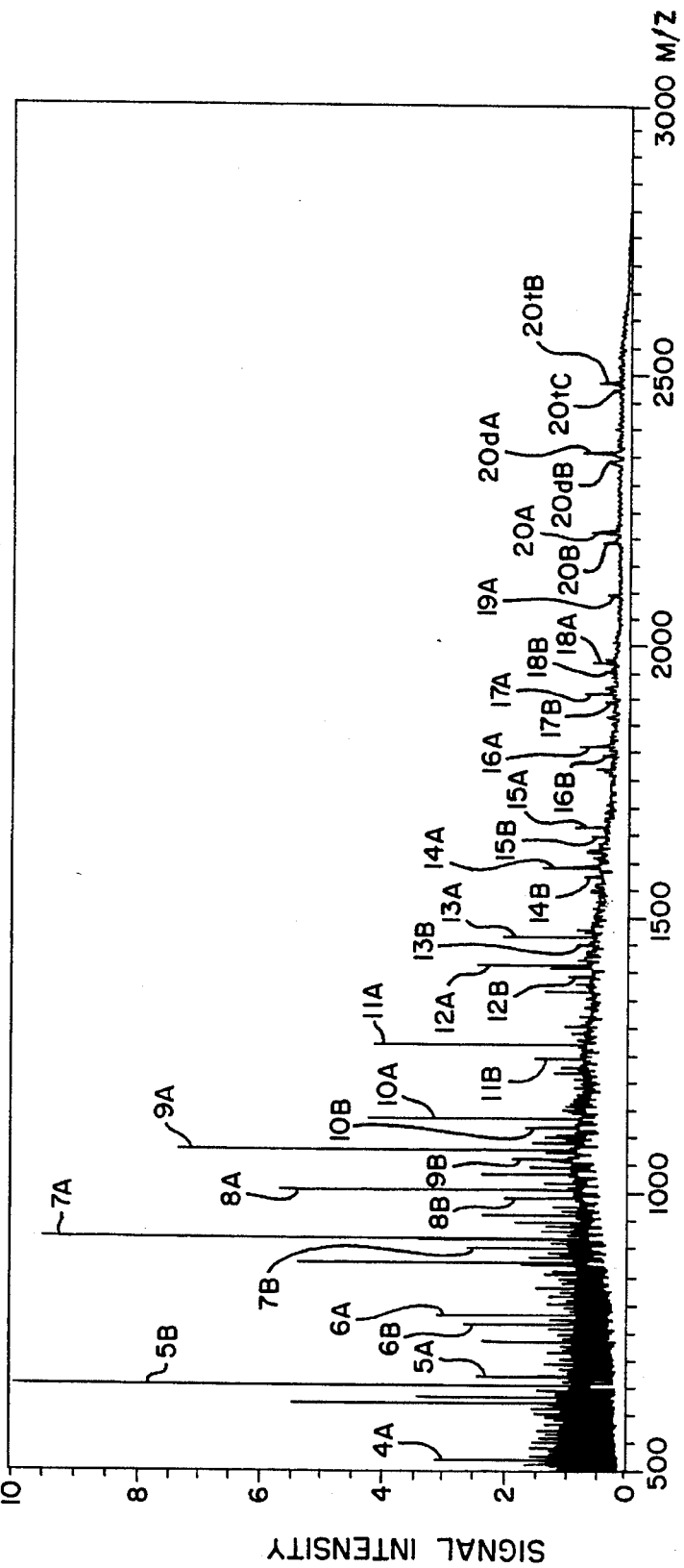
FIG. 26 is a diagram showing an analysis result of a reaction mixture which is treated by an acid anhydride for 5 hours at −18° C.

FIGS. 23–26 show analysis results in order to examine an effect of the reaction time interval during which the anhydride of the organic acid is applied, in the determination of the amino acid sequence. This example utilizes a sample peptide of sample No. 4 composed of 23 amino acids, which is treated by the anhydride of PFPA at −18° C. for 10 minutes (FIG. 23), 30 minutes (FIG. 24), one hour (FIG. 25) and 5 hours (FIG. 26). FIG. 22 shows an analysis result of the sample peptide of the sample No. 4 which is not treated by the anhydride of the organic acid, for comparison purposes.

When the sample is treated for 10 minutes (FIG. 23), there are detected the degraded peptides 1-22, 1-21, 1-20, 1-19, 1-18, 1-17, 1-16, 1-15, 1-14, 1-13, 1-12, 1-11, 1-10, 1-9 and 1-8, though an intensity of signals indicative of presence of the these sequential peptides is rather weak. Further, it is recognized that acylation occurs due to PFPA in the peptides 1-22 and 1-21.

When the sample is treated for 30 minutes (FIG. 24), there are detected peptides 1-20, 1-19, 1-18, 1-17, 1-16, 1-15, 1-14, 1-13, 1-12, 1-11, 1-10, 1-9, 1-8, 1-7, 1-6, 1-5 and 1-4. In this case, the acylation by PFPA is not perfect.

Further, when the sample is treated for one hour (FIG. 25) and five hours (FIG. 26), there are detected sufficient peptides each coupled with PFPA, i.e., 1-20, 1-19, 1-18, 1-17, 1-16, 1-15, 1-14, 1-13, 1-12, 1-11, 1-10, 1-9, 1-8, 1-7, 1-6, 1-5 and 1-4. Moreover, the intensity of respective signals is substantially at the same level under these two conditions. It is understood from these results that the anhydride of the organic acid is applied efficiently within 5 hours.

EXAMPLE 11

Figure 21:
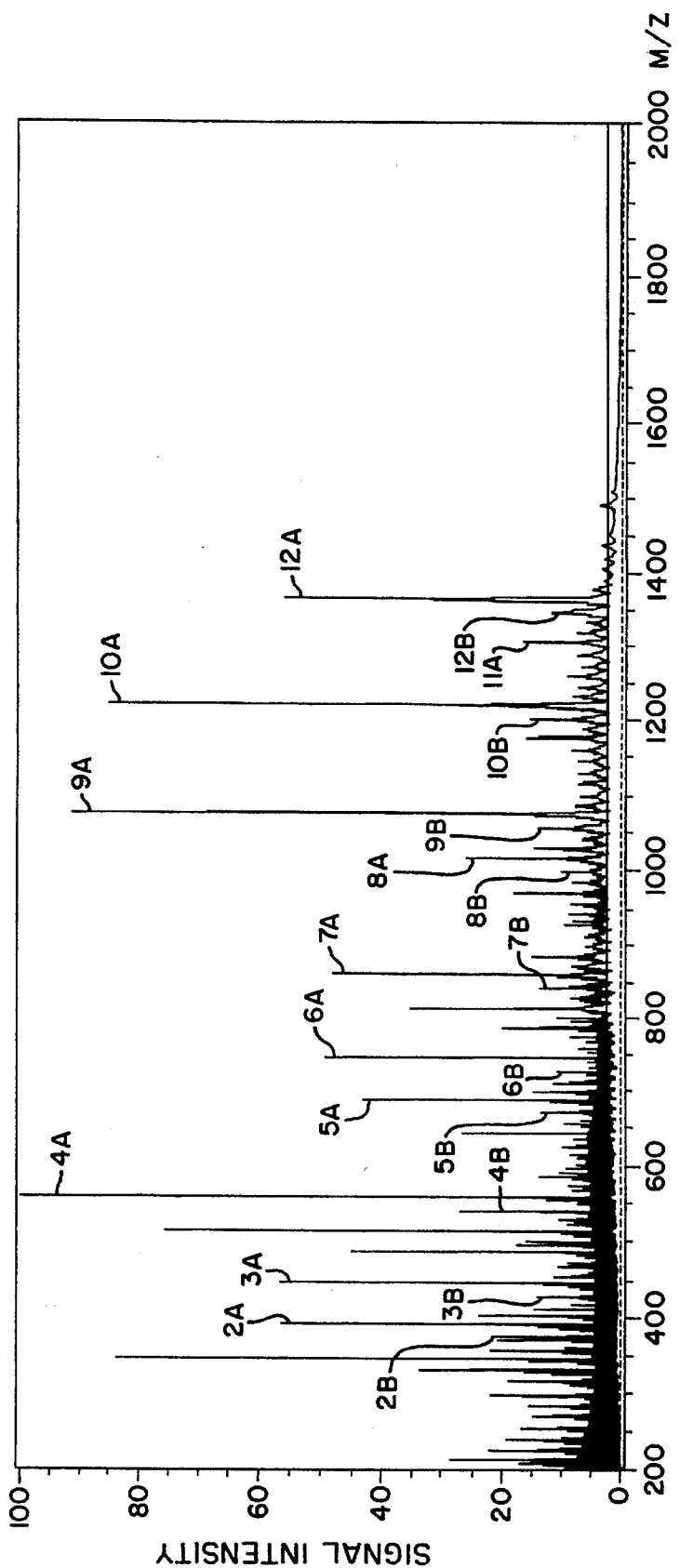
FIG. 21 is a diagram showing an analysis result of a reaction mixture which is treated by an acid anhydride for two hours at −18° C. and is then dried, and which is thereafter treated by water under a weak alkaline condition containing pyridine.

FIG. 21 shows an analysis result obtained such that a water is applied under a weak alkaline condition containing pyridine to a reaction mixture which is obtained by applying the anhydride of PFPA to dodecapeptide for two hours at −18° C. and then by drying the reaction product. As understood from the comparison to the FIG. 20 result, the detection intensity is lowered for sequential peptides 1-12, 1-11, 1-10, 1-9, 1-8, 1-7, 1-6, 1-5, 1-4. 1-3 and 1-2, those of which are coupled with PFPA and those of which lose one molecule of wafer. Thus, this treatment can facilitate analysis of the amino acid sequence.

The above described Examples 7–11 are summarized as follows. The dried peptide is treated by an anhydride of the organic acid represented by the general formula $CF_3—(CF_2)n—COOH$ (n is zero or more integer). The resulting reaction mixture is processed by FAB-MS to obtain a mass spectrum indicative of the whole peptide of the sample and a series of fragmented peptides produced by sequential degradation reaction of amino acids from the C-terminal of the sample peptide. The spectrum is analyzed to determine the amino acid sequence of the sample peptide from the C-terminal.

The anhydride of the organic acid is applied efficiently for less than 5 hours. The reaction temperature is set below 0° C. so as to suppress progression of subsidiary reaction. Further, after applying the anhydride of the organic acid, the reaction product is preferably treated by water so as to suppress dehydration peaks to thereby facilitate the analysis. Further, this method features that peak data analysis is facilitated for determination of the amino acid sequence since there is not detected a by-product peptide which would be produced by cleavage of peptide bond within the peptide chain.

The second aspect of the present invention features that protein or peptide is treated by an anhydride of the specific organic acid represented by the general formula $CF_3—(CF_2)n—COOH$ (n is zero or more integer) such as anhydride of trifluoroacetic acid (n=0), pentafluoropropionic acid (n=1) or heptafluorobutylic acid (n=2). By such treatment, amino acid sequence can be determined from the C-terminal of the protein or peptide by simplified processing without using an enzyme or other complicated compounds.

---

What is claimed is:

1. An analysis method comprising the steps of: applying to a protein or a peptide a vapor containing an organic acid selected from the group consisting of trifluoroacetic acid, pentafluoropropic acid, and heptafluorobutyric acid to cause the successive degradation of amino acids from a C-terminal of the protein or peptide so as to produce a reaction mixture; and analyzing the reaction mixture to determine an amino acid sequence of the protein or the peptide from a carboxyl-terminal thereof.

2. An analysis method according to claim 1; wherein the vapor applied to the protein or the peptide is obtained by vaporizing an aqueous solution containing 50–98% of the organic acid.

3. An analysis method according to claim 1; wherein the step of analyzing utilizes a mass spectrometer to process the reaction mixture to obtain a mass spectrum thereof so as to measure each chemical species contained in the reaction mixture.

4. An analysis method according to claim 1; wherein the step of analyzing utilizes an amino acid analyzer to process the reaction mixture to measure each chemical species contained in the reaction mixture.

5. An analysis method comprising the steps of:

applying to a protein or a peptide, an anhydride of an organic acid selected from the group consisting of trifluoroacetic acid, pentafluoropropic acid, and heptafluorobutyric acid, so as to produce a reaction mixture; and analyzing the reaction mixture to determine an amino acid sequence of the protein or the peptide from a carboxy-terminal thereof.

6. An analysis method according to claim 5; wherein the anhydride of the organic acid is applied to the protein or the peptide in the form of a solution thereof in a volatile organic solvent.

7. An analysis method according to claim 5; wherein the anhydride of the organic acid is applied to the protein or the peptide at a temperature below 0° C.

8. An analysis method according to claim 5; wherein the anhydride of the organic acid is applied to the protein or the peptide for a time interval less than 5 hours.

9. An analysis method according to claim 5; including the step of treating the reaction mixture with a water or a steam to produce a reaction product before the step of analyzing.

10. An analysis method according to claim 9; wherein the step of analyzing utilizes a mass spectrometer to obtain a mass spectrum of the reaction product.

11. An analysis method comprising the steps of:

applying to a protein or a peptide an anhydride of an organic acid selected from the group consisting of trifluoroacetic acid, pentafluoropropic acid and heptafluorobutyric acid, at a temperature below 0° C., to cause successive degradation of an unreacted carboxy-terminal of the protein or peptide so as to produce a reaction mixture; and analyzing the reaction mixture to determine an amino acid sequence of the protein or the peptide from a carboxy-terminal thereof.

12. An analysis method according to claim 11; wherein the anhydride of the organic acid is applied to the protein or the peptide in the form of a solution thereof in a volatile organic solvent.

13. An analysis method according to claim 11; wherein the step of analyzing comprises analyzing the reaction mixture with a mass spectrometer to obtain a mass spectrum thereof to enable measurement of each chemical species contained in the reaction mixture.

14. An analysis method according to claim 11; wherein the step of analyzing comprises analyzing the reaction mixture with an amino acid analyzer to enable measurement of each chemical species contained in the reaction mixture.

15. A method for performing an amino acid sequence analysis of a protein or a peptide from a carboxy-terminal thereof in the absence of an enzyme, comprising the steps of:

applying to a protein or a peptide which has not been modified by thiohydantoin processing, an organic acid selected from the group consisting of trifluoroacetic acid, pentafluoropropic acid and heptafluorobutyric acid so as to produce a reaction mixture; and analyzing the reaction mixture utilizing mass spectrometry to determine an amino acid sequence of the protein or the peptide from a carboxy-terminal thereof.

16. An analysis method according to claim 15; wherein the organic acid is in the form of an anhydride thereof which is applied to the protein or the peptide in a solution comprising a volatile organic solvent.

17. An analysis method according to claim 16; wherein the anhydride of the organic acid is applied to the protein or the peptide at a temperature below 0° C.

18. An analysis method according to claim 17; wherein the anhydride of the organic acid is applied to the protein or the peptide for a time interval less than 5 hours.

19. An analysis method according to claim 15; including the step of treating the reaction mixture with water or steam to produce a reaction product before the step of analyzing.

\* \* \* \* \*